US010391135B2

(12) United States Patent
Alcantar et al.

(10) Patent No.: US 10,391,135 B2
(45) Date of Patent: Aug. 27, 2019

(54) INHIBITION OF FORMATION OF AMYLOID β-PROTEIN FIBRILS USING CACTUS MUCILAGE EXTRACTS

(71) Applicants: Norma A. Alcantar, Tampa, FL (US); David Morgan, Clearwater, FL (US); Zeinab Veisi, Tampa, FL (US); Leonid Breydo, Tampa, FL (US); Vladimir N. Uversky, Tampa, FL (US); Ryan G. Toomey, Tampa, FL (US); Tunan Peng, Odessa, FL (US); Eva Stephanie Lobbens, Farum (DK)

(72) Inventors: Norma A. Alcantar, Tampa, FL (US); David Morgan, Clearwater, FL (US); Zeinab Veisi, Tampa, FL (US); Leonid Breydo, Tampa, FL (US); Vladimir N. Uversky, Tampa, FL (US); Ryan G. Toomey, Tampa, FL (US); Tunan Peng, Odessa, FL (US); Eva Stephanie Lobbens, Farum (DK)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 15/706,086

(22) Filed: Sep. 15, 2017

(65) Prior Publication Data

US 2018/0078595 A1   Mar. 22, 2018

Related U.S. Application Data

(60) Provisional application No. 62/395,786, filed on Sep. 16, 2016.

(51) Int. Cl.
*A61K 36/00* (2006.01)
*A61K 36/33* (2006.01)
*A61K 9/00* (2006.01)

(52) U.S. Cl.
CPC ............ *A61K 36/33* (2013.01); *A61K 9/0085* (2013.01); *A61K 2236/15* (2013.01); *A61K 2236/331* (2013.01); *A61K 2236/53* (2013.01)

(58) Field of Classification Search
None
See application file for complete search history.

(56) References Cited

U.S. PATENT DOCUMENTS

| 9,163,374 B2 | 10/2015 | Alcantar et al. |
| 2001/0055630 A1* | 12/2001 | Castillo ............... A61K 31/215 424/769 |

FOREIGN PATENT DOCUMENTS

CN   102432690 A  *  5/2012

OTHER PUBLICATIONS

El-Mostafa, K., El Kharrassi, Y., Badreddine, A., Andreoletti, P., Vamecq, J., El Kebbaj, M. S., Latruffe, N., Lizard, G., Nasser, B. and Cherkaoui-Malki, M., Nopal Cactus (*Opuntia ficus-indica*) as a Source of Bioactive Compounds for Nutrition, Health and Disease. Molecules, 2014. 19(9): p. 14879-p. 14901.
Moran-Ramos, S., Avila-Nava, A., Tovar, A. R., Pedraza-Chaverri, J., Lopez-Romero, P. and Torres, N., Opuntia ficus indica (nopal) attenuates hepatic steatosis and oxidative stress in obese Zucker (fa/fa) rats. The Journal of Nutrition, 2012(11): p. 1956.
Mahouachi, M., Atti, N. and Hajji, H., Use of Spineless Cactus (*Opuntia ficus indica* f. *inermis*) for Dairy Goats and Growing Kids: Impacts on Milk Production, Kid's Growth, and Meat Quality. Scientific World Journal, 2012.
Ortiz-Rodriguez, R., Valdez-Alarcon, J. J., Gomez-Ramos, B., Lopez-Medina, J., Chavez-Moctezuma, M. P., Garcia-Saucedo, P. A. and Perez-Sanchez, R. E., Yield and microbiological quality of raw milk and fresh cheese obtained from holstein cows receiving a diet supplemented with nopal (*Opuntia ficus-indica*). African Journal of Microbiology Research, 2012. 6(14): p. 3409-3414.
Agyare, C., Boakye, Y. D., Bekoe, E. O., Hensel, A., Dapaah, S. O. and Appiah, T., Review: African medicinal plants with wound healing properties. Journal of Ethnopharmacology, 2016. 177: p. 85-100.
Antunes-Ricardo, M., Gutierrez-Uribe, J. A., Lopez-Pacheco, F., Alvarez, M. M. and Serna-Saldivar, S. O., In vivo anti-inflammatory effects of isorhamnetin glycosides isolated from *Opuntia ficus-indica* (L.) Mill cladodes. Industrial Crops and Products, 2015. 76: p. 803-808.
El Kossori, R. L., Villaume, C., El Boustani, E., Sauvaire, Y. and Mejean, L., Composition of pulp, skin and seeds of prickly pears fruit (*Opuntia ficus indica* sp.). Plant Foods for Human Nutrition (Dordrecht), 1998. 52(3): p. 263-270.
Sluchanko, N. N. and Uversky, V. N., Hidden disorder propensity of the N-terminal segment of universal adapter protein 14-3-3 is manifested in its monomeric form: Novel insights into protein dimerization and multifunctionality. Biochimica Et Biophysica Acta—Proteins and Proteomics, 2015. 1854(5): p. 492-504.
Breydo, L., Newland, B., Zhang, H., Rosser, A., Werner, C., Uversky, V. N. and Wang, W., A hyperbranched dopamine-containing PEG-based polymer for the inhibition of alpha-synuclein fibrillation. Biochemical and biophysical research communications, 2016. 469(4): p. 830-5.
Kutyshenko, V. P., Beskaravayny, P. and Uversky, V. N., "In-plant" NMR: Analysis of the Intact Plant *Vesicularia dubyana* by High Resolution NMR Spectroscopy. Molecules, 2015. 20(3): p. 4359-4368.
Uversky, V. N., The multifaceted roles of intrinsic disorder in protein complexes. Febs Letters, 2015. 589(19): p. 2498-2506.
Portillo, A., Hashemi, M., Zhang, Y., Breydo, L., Uyersky, V. N. and Lyubchenko, Y. L., Role of monomer arrangement in the amyloid self-assembly. Biochimica Et Biophysica Acta—Proteins and Proteomics, 2015. 1854(3): p. 218-228.
Breydo, L. and Uversky, V. N., Structural, morphological, and functional diversity of amyloid oligomers. Febs Letters, 2015. 589(19): p. 2640-2648.

(Continued)

*Primary Examiner* — Qiuwen Mi
(74) *Attorney, Agent, or Firm* — Michele L. Lawson; Smith & Hopen, P.A.

(57) ABSTRACT

A method of treating an amyloid disease by administration of cactus mucilage extract from *Opuntia ficus-indicia* is presented. Both gelling and non-gelling cactus mucilage extracts were found to induce changes in the secondary structures of the amyloid beta peptides thus interfering with formation of Aβ fibrils and aggregation of Aβ fibrils into plaques.

4 Claims, 17 Drawing Sheets

(56) References Cited

OTHER PUBLICATIONS

Calcul, L., Zhang, B., Jinwal, U. K., Dickey, C. A. and Baker, B. J., Natural products as a rich source of tau-targeting drugs for Alzheimer's disease. Future Med Chem, 2012. 4(13): p. 1751-61.

Doig, A. J. and Derreumaux, P., Inhibition of protein aggregation and amyloid formation by small molecules. Current Opinion in Structural Biology, 2015. 30: p. 50-56.

Hu, P., Li, Z., Chen, M., Sun, Z., Ling, Y., Jiang, J. and Huang, C., Structural elucidation and protective role of a polysaccharide from Sargassum fusiforme on ameliorating learning and memory deficiencies in mice. Carbohydrate Polymers, 2016. 139: p. 150-158.

Liu, H., Ojha, B., Morris, C., Jiang, M., Wojcikiewicz, E. P., Rao, P. P. N. and Du, D., Positively Charged Chitosan and N-Trimethyl Chitosan Inhibit A beta 40 Fibrillogenesis. Biomacromolecules, 2015. 16(8): p. 2363-2373.

Zhang, H., Cao, Y., Chen, L., Wang, J., Tian, Q., Wang, N., Liu, Z., Li, J., Wang, N., Wang, X., Sun, P. and Wang, L., A polysaccharide from Polygonatum sibiricum attenuates amyloid-beta-induced neurotoxicity in PC12 cells. Carbohydrate Polymers, 2015. 117: p. 879-886.

Li, X. Z., Zhang, S. N. Liu, S. M. and Lu, F., Recent advances in herbal medicines treating Parkinson's disease. Fitoterapia, 2013. 84: p. 273-85.

Caruana, M. and Vassallo, N., Tea Polyphenols in Parkinson's Disease. Adv Exp Med Biol, 2015. 863: p. 117-37.

Fazili, N. A. and Naeem, A., Anti-fibrillation potency of caffeic acid against an antidepressant induced fibrillogenesis of human alpha-synuclein: Implications for Parkinson's disease. Biochimie, 2015. 108: p. 178-85.

Goldberg, M. S. and Lansbury, P. T., Jr., Is there a cause-and-effect relationship between alpha-synuclein fibrillization and Parkinson's disease? Nat Cell Biol, 2000. 2(7): p. E115-119.

Fink, A. L., The aggregation and fibrillation of alpha-synuclein. Acc Chem Res, 2006. 39(9): p. 628-34.

Breydo, L., Wu, J. W and Uversky, V. N., Alpha-synuclein misfolding and Parkinson's disease. Biochim Biophys Acta, 2012. 1822(2): p. 261-85.

Uversky, V. N. and Eliezer, D., Biophysics of Parkinson's disease: structure and aggregation of alpha-synuclein. Curr Protein Pept Sci, 2009. 10(5): p. 483-99.

Alcantar NA, Aydil ES and Israelachvili NJ, Polyethylene glycol coated biocompatible surfaces. J Biomed Mater Res, 2000. 51(3): p. 343-351.

Drummond, C., Alcantar, N. and Israelachvili, J., Shear alignment of confined hydrocarbon liquid films. Physical Review E, 2002. 66(1).

Sarroukh, R., Cerf, E., Derclaye, S., Dufrene, Y. F., Goormaghtigh, E., Ruysschaert, J.-M. and Raussens, V., Transformation of amyloid beta(1-40) oligomers into fibrils is characterized by a major change in secondary structure. Cellular and Molecular Life Sciences, 2011. 68(8): p. 1429-1438.

Walsh, D. M., Hartley, D. M., Kusumoto, Y., Fezoui, Y., Condron, M. M., Lomakin, A., Benedek, G. B., Selkoe, D. J. and Teplow, D. B., Amyloid beta-protein fibrillogenesis—Structure and biological activity of protofibrillar intermediates. Journal of Biological Chemistry, 1999. 274(36): p. 25945-25952.

Stine, W. B., Dahlgren, K. N., Krafft, G. A. and LaDu, M. J., In vitro characterization of conditions for amyloid-beta peptide oligomerization and fibrillogenesis. Journal of Biological Chemistry, 2003. 278(13): p. 11612-11622.

Dahlgren, K. N., Manelli, A. M., Stine, W. B., Baker, L. K., Krafft, G. A. and LaDu, M. J., Oligomeric and fibrillar species of amyloid-beta peptides differentially affect neuronal viability. Journal of Biological Chemistry, 2002. 277(35): p. 32046-32053.

Jimenez, J., M.S. Thesis (Major Professor: Norma Alcantar): Systematic study of amyloid beta peptide conformations implications for AD. vol. M.S. 2005, Tampa: USF.

Selenica, M. L., Wang, X., Ostergaard-Pedersen, L., Westlind-Danielsson, A. and Grubb, A., Cystatin C reduces the in vitro formation of soluble A beta 1-42 oligomers and protofibrils. Scandinavian Journal of Clinical & Laboratory Investigation, 2007. 67(2): p. 179-190.

\* cited by examiner

| Concentration | Lag Phase |
|---|---|
| GE extract control 0.25 mg/mL | No fibrillation |
| Alpha-synuclein control 0.25 mg/mL | 10.0 ± 0.7 hours |
| 0.25 mg/mL | No fibrillation |
| 0.125 mg/mL | No fibrillation |
| 0.0625 mg/mL | No fibrillation |
| 0.015625 mg/mL | No fibrillation |
| 0.007812 mg/mL | 19.3 ± 3.9 hours |
| 0.000390625 mg/mL | 14.5 ± 0.7 hours |

| Concentration | Lag Phase |
|---|---|
| NE extract control 0.25 mg/mL | No fibrillation |
| Alpha-synuclein control 0.25 mg/mL | 10.0 ± 0.7 hours |
| 0.25 mg/mL | No fibrillation |
| 0.125 mg/mL | No fibrillation |
| 0.0625 mg/mL | No fibrillation |
| 0.015625 mg/mL | 14.5 ± 1.2 hours |
| 0.007812 mg/mL | 14.6 ± 0.2 hours |
| 0.000390625 mg/mL | 13.2 ± 0.5 hours |

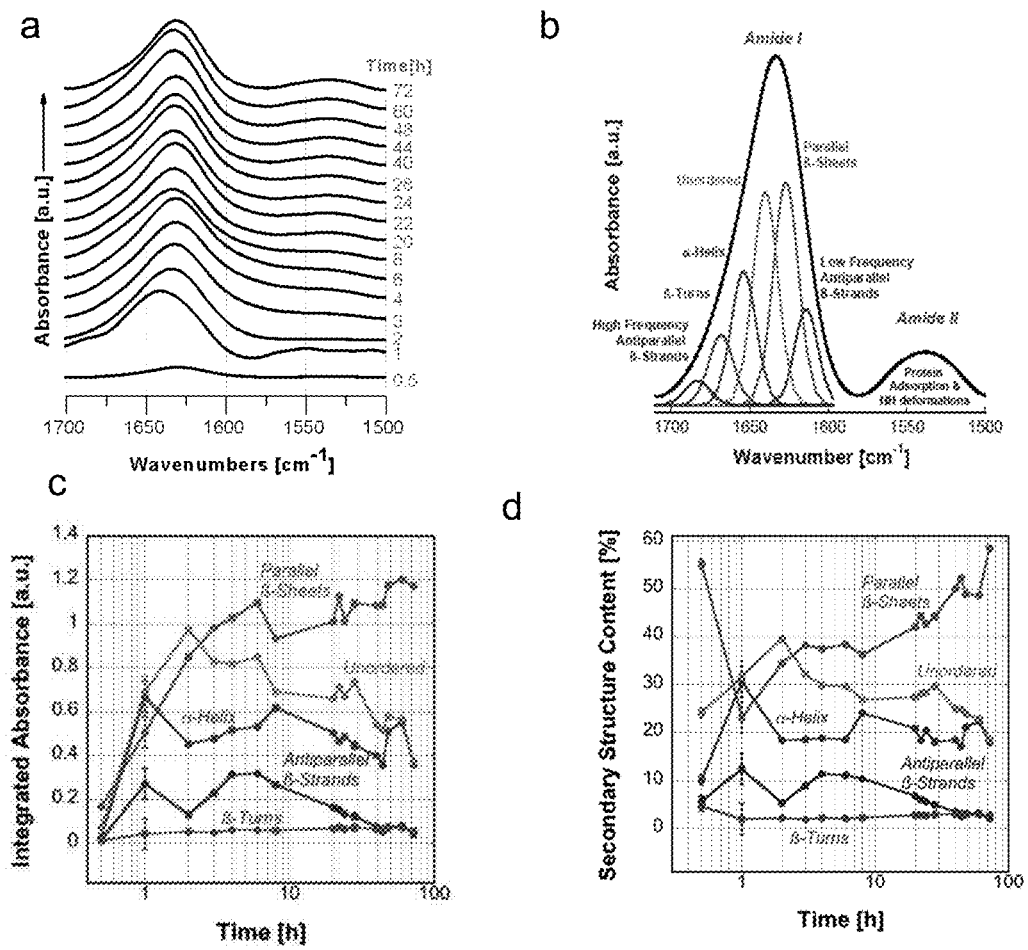
FIG. 31A-D

INHIBITION OF FORMATION OF AMYLOID β-PROTEIN FIBRILS USING CACTUS MUCILAGE EXTRACTS

CROSS-REFERENCE TO RELATED APPLICATIONS

This application claims priority to U.S. Provisional Patent Application No. 62/395,786, entitled "Inhibition of Formation of Amyloid B-Protein Fibrils Using Cactus Mucilage Extracts", filed by the same inventors on Sep. 16, 2016, the contents of which are herein incorporated by reference.

FIELD OF INVENTION

This invention relates to treating amyloid neuronal diseases. Specifically, the invention addresses treating amyloid protein diseases cactus mucilage.

BACKGROUND OF THE INVENTION

Alzheimer's disease (AD) is the primary cause of senile dementia worldwide. It is a neurodegenerative disorder defined by the loss of memory and language skill, collapse of the cognitive function, and distortion of social behavior. As of today, the onset mechanisms of Alzheimer' s disease and cure are unknown. However, three hallmarks are commonly encountered: extra and intracellular accumulation of amyloid beta peptide plaques, formation of intracellular neurofibrillary tangles, and inevitable neuronal death. This research is focused on using cactus mucilage to induce the dispersion of Amyloid Beta (Aβ) peptide fibers in order to interrupt the kinetic formation mechanisms of Aβ plaques.

Alzheimer's disease (AD) is a chronic dementia characterized by the presence of dense bundles of unusual fibrils within the cerebral cortex and hippocampus, termed senile or amyloid plaques. From a structural standpoint, amyloid plaques consist of large numbers of fibrils that are made up primarily of amyloid beta (Aβ) peptides assembled in parallel-pleated sheet configurations. These hierarchic structures are one of the hallmarks of AD.

The ability of a natural material containing high amounts of glyconutrients to disrupt Aβ fibril formation was investigated. The extracts of the *Opuntia ficus-indica* (OFI, also known as prickly pear or nopal cactus) are a combination of polysaccharides (i.e., glycans or sugars) such as n-acetylneuraminic acid, fucose, arabinose, mannose, galactose, rhamnose, xylose, and glucose, to name a few.[1] These compounds have been known to present anti-inflammatory properties, enhance tissue regeneration, disperse high molecular weight compounds, and participate in brain development and learning (as some of these sugars also are found in whey protein and breast milk).[2-5]

The effectiveness of cactus mucilage extracted from *Opuntia ficus-indica* in disturbing the aggregation pathway of Amyloid β-Protein (Aβ) fibrils was analyzed. Mucilage is a pectin polysaccharide with a backbone of α-D-galacturonic acid and β-L-rhamnose and a branch of arabinose or xylose. Two different fractions of mucilage can be extracted: pectin gelling extract which forms gels in the presence of Ca2+ ions (GE) and non-gelling extract (NE). The effectiveness of mucilage in disturbing the formation of Aβ fibrils was evaluated. Aβ monomeric species have been incubated along with different concentration of the mucilage extract in vitro. The aggregation kinetics of the Aβ proteins were monitored by Fourier transform infrared (FTIR) spectroscopy. Transmission electron microscopy (TEM) was used to monitor the aggregation process and fibril morphology. Our results indicate that introducing mucilage induces changes in the secondary structures of the Aβ peptides and results in amyloid detribalized structures. Our experimental results support the effectiveness of cactus mucilage in interfering with protein accumulation pathway and targeting the Aβ plaques.

The mucilage is optionally administered into the CNS. Useful methods of administration include pumps designed to infuse materials into the ventricles. These pumps are implanted subcutaneously and can be refilled with a syringe. Power to the pumps is provided by batteries, which are replaced occasionally.

BRIEF DESCRIPTION OF THE DRAWINGS

For a fuller understanding of the invention, reference should be made to the following detailed description, taken in connection with the accompanying drawings, attached hereto.

FIG. 31A-D is a series of images depicting the time evolution of $A\beta_{42}$ fibril growth by ATR-FTIR. (a) absorbance spectra. (b) example of Gaussain deconvolution. (c) kinetic analysis of the peptide secondary structure conformational changes after deconvolution. Parallel β-sheets dominate the fibril formation, whereas antiparallel β-structures disappear as fibrils grow into plaques. (d) If only the peak positions from the second derivative of each spectrum are used, the secondary structure content is calculated. Both Figures c and d indicate that parallel β-sheets dominate the fibrillation process of $A\beta_{42}$. The α-helix structure shows to vary only during the first two hours and then remains fairly constant.

DETAILED DESCRIPTION OF THE PREFERRED EMBODIMENT

Figure 1:
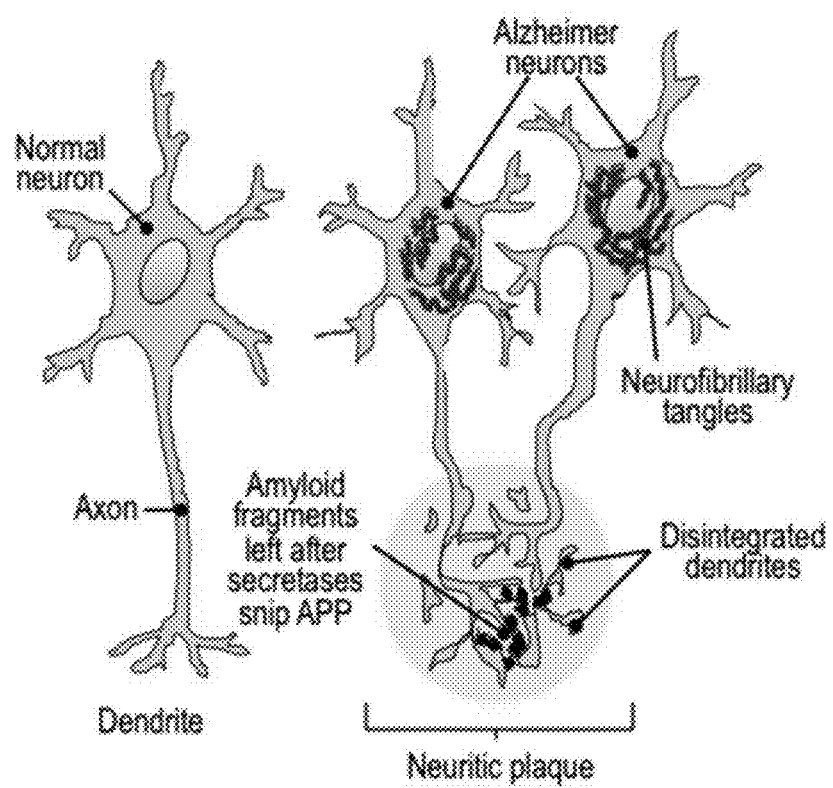
FIG. 1 is an image depicting neuritic plaques in Alzheimer's disease.

As used herein, "treat", "treatment", "treating", and the like refer to acting upon a condition, such as a neurodegenerative disease, with an agent depending on the desired effect, to affect the condition by improving or altering it. The improvement or alteration may include an improvement in symptoms or an alteration in the physiologic pathways associated with the condition. "Treatment," as used herein, covers one or more treatments of a condition in a host (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., reduce inflammation).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as antibodies or other agents which are effective for producing an intended result, including preventing further autoimmune disease or immunotolerance, or treating an autoimmune disease, such as rheumatoid arthritis and asthma, or immunotolerance, such as cancer. Compositions according to the present invention may be used to effect a favorable change on immune cells, whether that change is an improvement, such as stopping or reversing the immune disease, or relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" refers to introducing an agent of the present disclosure into a patient. One preferred route of administration of the agent is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, the term "subject," "patient," or "organism" includes humans and mammals (e.g., mice, rats, pigs, cats, dogs, and horses). Typical patients to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Cactus mucilage is a biomaterial comprised of sugars and carbohydrates extracted from cactus plants. It is renewable, biodegradable, abundant, and of low cost. Previous research has found that cactus mucilage is an effective dispersant of heavy aliphatic and aromatic molecules such as those found in crude oil. In this study, Aβ monomeric species have been incubated along with cactus mucilage. The changes in the kinetic formation of the Aβ fibers were monitored using Attenuated Total Reflectance Fourier Transform Infrared (ATR-FTIR) spectroscopy. Different concentrations and types of mucilage fractions have been tested to determine the changes induced by cactus mucilage in the secondary structures of the Aβ peptides during and after the incubation process. Different techniques, such as optical microscopy, atomic force microscopy, and transmission electron microscopy; have been used to capture the topology of the different processes of aggregation and dispersion in terms of adhesion, size evolution, and distribution of the peptide. In addition, the Du Noüy ring method test has been used to determine the surface energy of the fibers/mucilage complex.

Example 1

Mucilage was extracted from the fresh cactus pads as a gelling extract (GE) and a non-gelling extract (NE). The pads were washed, dried and weighed. The pads were diced or peeled and boiled for 20 min, then the mixture was liquidized in a blender (Osterizer™, Sunbeam Products, Inc., Boca Raton, Fla.). 1M sodium hydroxide (NaOH) was added to neutralize the mixture and then centrifuged to separate the supernatant, which contains the NE, from the solid precipitate, containing the GE. Before the GE was extracted, the non-gelling extract (NE) was removed. The GE was then extracted using an adaptation of a method developed by Turquois et al. (Turquois, et al. Extraction of highly gelling pectic substances from sugar beet pulp and potato pulp: influence of extrinsic parameters on their gelling properties. *Food Hydrocolloids* 1999, 13, (3), 255-262). The solids were mixed with 7.5 g/L sodium hexametaphosphate [$(NaPO_3)_6$] in 50 mM NaOH, in a 1:1 mass-to-volume ratio of solids to solution. The mixture was stirred for 1 h, then vacuum filtered with knitted polyester cloth (Polx 1200, Berkshire Corp., Great Barrington, Mass.) or to obtain the filtrate. The filtrate pH was lowered to 2 using hydrochloric acid (HCl) and refrigerated overnight (~5° C.) in order to precipitate the GE. The precipitate was separated by centrifugation, re-suspended in sufficient deionized (DI) water to cover the pellet, and the pH adjusted to 8.0 with 1M NaOH to re-dissolve the precipitate. The resulting solution was purified by successive filtering through a 1.2 μm and a 0.45 μm membrane. The GE was re-precipitated with acetone or isopropanol in a 2:3 liquid-to-solvent volume-to-volume ratio, then washed with alcohol and dried under ambient conditions.

The non-gelling extract (NE) was collected as described above, and sodium chloride added to the supernatant to form a final concentration of 1M NaCl. The supernatant was filtered with knitted polyester cloth (Polx 1200, Berkshire Corp., Great Barrington, Mass.) or Whatman 41 filter paper, based on the viscosity of the liquid, to obtain the filtrate. Acetone or isopropanol was added in a 2:3 volume-to-volume ratio of supernatant to solvent to precipitate the NE. The precipitate was washed with ethanol-water mixtures in a graded series (70%, 80%, 90%, 95% ethanol, and absolute ethanol) to remove any remaining impurities. The precipitate was left to dry at room temperature overnight, followed by an overnight drying in an air oven (Yamato DX-41, Japan).

Example 2

Results and Discussion:

Experimental analysis of ATR-FTIR spectra and the topology of the Aβ fibers indicate that the addition of dispersion concentration of cactus mucilage has an effect in the surface energy of normal Aβ fibers. The inventors have also seen that the kinetic formation of Aβ fibers is slightly disturbed by the presence of mucilage.

Conclusions:

These positive experimental results could possibly provide basic information of an alternative method to treat the formation of Alzheimer's disease plaques.

Example

Studies of a protein aggregation essay using recombinant α-synuclein was converted to amyloid fibrils in the presence of different concentrations of OFI showed that the lag phase of α-synuclein fibril formation was significantly increased. More interestingly, it was observed that one of the OFI extracts completely inhibited the amyloid fibril formation process at mass ratios of 1:20 extract/protein. Therefore, OFI fractions were tested for the potential to reduce adverse effects of the development of AD by disrupting protein aggregation that caused neuronal death. Such effect can be evaluated in terms of the level of fibril development or disruption using a protein aggregation essay, scanning electron microscopy (SEM), atomic force microscopy (AFM), and attenuated total reflection Fourier transform infrared (ATR-FTIR) spectroscopy. It also is necessary to isolate the compounds of OFI that are responsible for inhibiting protein aggregation with analytical techniques used for polysaccharides' characterization.

Specific Aim 1. Identify the Conditions at which Polysaccharides from Cactus Extracts can Destabilize Amyloid Fiber Formation.

Extracts from the OFI cactus contain myriad high, medium, and low molecular weight polysaccharides (i.e, monosaccharides, oligosaccharides, and large polysaccharides). In these experiments, the inventors will separate cactus extracts from the solid parts (i.e., gelling extracts, GE), non-gelling extracts (NE) from the liquid fractions, or combined extracts (both GE and NE). It is known that these extracts contain plant glyconutrients, but their active molecules differ from each extract because they originate from fractions of the cactus with different functions. The inventors will verify that the integrity of the plant extracts is maintained from characterization data of the intact plant. The inventors will track a range of concentrations from nanograms to milligrams of cactus extracts that show a destabilizing effect on Aβ fibril formation. Using an automated protein aggregation assay, the inventors will be able to obtain the optimal concentration of cactus extracts that can induce disorder in Aβ fibrils and that can disperse amyloid aggregates. These reactions also will be followed with ATR-FTIR spectroscopy, SEM, and AFM. Apart from being able to elucidate molecular information on the kinetic disruption mechanisms of the plaques due to the addition of a cactus extract type, the inventors also will compare and corroborate what conditions and dosage of cactus extracts affect the amyloid formation from the protein aggregation essay data.

Specific Aim 2. Separate and Characterize the Polysaccharides Responsible for Aβ Fibrils Disruption.

In these experiments, the inventors will separate the individual components of the extract that can inhibit protein aggregation at the lowest concentrations. Natural polysaccharides will be categorized by physical properties such as size and by functionality. The inventors will compare our findings against commercially-available pure glycans and, for the compounds that are not available, the inventors will synthesize the identified polysaccharides by Aldolase-Catalyzed Condensation reactions. Synthetic copies of such polysaccharides also will be tested against the efficacy and quality of the OFI natural extracts. ATR-FTIR and high-performance liquid chromatography (HPLC) with a refractive index detector specific for sugars will be used to determine distinct polysaccharides components, their chemistry, and their functionality. Gel Permeation Chromatography (GPC) will be used to determine molecular size and average molecular weights. Specific subfractions and individual sugars of each extract will then be tested and characterized to determine their efficacy at the range of concentrations that worked well from Aim 1 using the protein aggregation essay.

This proposal is high risk/high impact because isolating specific active compounds from natural plants is challenging. However, if the inventors are able to determine the specific polysaccharide(s) that impact the formation of senile plaques, the potential to develop future therapies with natural materials capable of efficient and effective means of clearing Aβ plaques will be imminent.

Example 3

This study focuses on extracts from the *Opuntia ficus-indica* (OFI) or prickly pear (i.e., nopal) to disrupt the formation of amyloid beta (Aβ) fibrils into AD plaques. OFI is an edible, perennial, succulent cactus plant that belongs to the Opuntioideae family. This type of cacti is edible and already used in FDA-approved medications (NDC Codes: 59535-0131-1, 59535-1311-1, 15631-0322-0, 15631-0322-1, 15631-0322-2, 15631-0322-3).[6] In addition, the FDA Office of Food Labeling registered Nopalacrin™ as a food supplement (produced by 4R Health Products™; Nopalacrin™ contains 500 mg of nopal/capsule, 90 capsules per bottle).[7] Several published studies also reported the benefits of OFI in feeding animals.[8-10] Although the implementation of OFI and its extracts for AD therapies must first be tested in vivo and then in clinical trials, it considered safe for human and animal consumption. The hierarchical organization from the simple to the whole Opuntioideae are very well established, so this will allow us to work exclusively with the OFI, but transfer our findings to glyconutrients (i.e., essential sugars) from other *Opuntia*-like species.[1] The prickly pear can be consumed raw or cooked.[11,12] Extensive work by the PI's research group has shown that the viscous part of the OFI (cactus mucilage) effectively purifies water in a number of polluted environments, as the OFI mucilage flocculates both bacteria and sediments,[13-15] removes heavy metals[7,16] and radioactive ions,[17] and effectively disperses crude oil.[18] The cactus plant also has been used in ancient cultures as an alternative therapy to enhance cognition and memory, expedite tissue healing,[2] and reduce tissue inflammation.[3,4,19,20] OFI plants are drought-resistant, growth extremely quickly,[1] and are adaptable to hot and cold climates.[21] OFI consistently contain a mixture of approximately 55 various molecular-weight glycan residues composed basically of arabinose (67.3%), galactose (6.3%), rhamnose (5.4%), and xylose (20.4%).[14,16,22,23]

The rationale for using OFI to disrupt amyloid senile plaques was conceived by looking at the effect of the cactus to disperse crude oil.[24] The composition of crude oil varies depending on the region, but, on average, consists of paraffins, naphthenes, aromatics, resins, and asphaltic compounds in different percentages.[25] However, the OFI mucilage can disperse these heavy hydrocarbon chains and metal-organic compounds analogously to commercial dispersants such as Corexit®.[26-28] The premise is that the OFI exhibits unique amphiphilic structures that can access insoluble heavy organic chains as well as low molecular oil fractions to create stable oil/water emulsions. Similarly, the inventors hypothesize that the unique amphiphilic polysaccharides from the cactus plant will bind amyloid fibrils via both hydrophobic and hydrophilic interactions with the individual amino acids of amyloid beta (Aβ) peptides. That is, the polysaccharides of the OFI will bind both hydrophilic amino acid stretches (through hydrogen bonds) and aliphatic moieties (through hydrophobic interactions), effectively stabilizing Aβ/OFI extract emulsions, and solubilizing Aβ polypeptides from AD plaques. The hierarchical structure of OFI is highly stable and comprises low, medium, and high molecular weight glycans or polysaccharides. To the best of our knowledge, the OFI contains more glyconutrients than any other single plant on Earth, including Aloe vera.[29,30]

The aggregation kinetics of fibril disruption will be followed by two independent techniques: (1) ATR-FTIR spectroscopy will monitor the chemical conformations of the peptides interactions with polysaccharides and (2) protein aggregation followed with time-resolved thioflavin-T (ThT) fluorescence spectroscopy will provide unequivocal in vitro data of OFI extract kinetic concentrations and fibril time-growth development. Both coPIs are experts in the pathology of amyloid-type proteins and in studying protein aggregation.[31-38] TEM, SEM, and AFM will be used to monitor the aggregation/disruption process of fibril morphology. These techniques will provide direct confirmation of Aβ fibril disruption as well as information on how OFI natural compounds are intrinsically involved in the kinetic process. Furthermore, our findings will lead to identifying the extent to which natural polysaccharides can modify Aβ secondary structure and determining what the impact of this mechanism might be in relation to other biological mechanisms of defibrillation for a later smooth transition into testing in mouse models and patients.

Some natural products have been found to inhibit the amyloid fibril formation of different proteins,[39] and several compounds have shown to have an effect against Parkinson's and Alzheimer's diseases.[40-46] Nonetheless, results exhibit high variability in the data, and the effective concentration of polysaccharides is relatively high with respect to the amyloid peptide concentration. In particular, polysaccharides from *Sargassum fusiforme* (brown alga) have been isolated and tested in animal models. The oral dosage was on the order of 250 mg/kg for 21 days in male ICR mice (20±2 g). Although the results show a slight gain in cognition for some of the animals that consume polysaccharides, the work does not correlate polysaccharides to amyloid beta fibrils dissolution.[41] Liu et al. discussed the possible interaction of amyloid peptides with positively-charged, flexible molecules derived from chitosan and $A\beta_{40}$ fibrils, although the best concentration to inhibit fibrillation was found to be 0.5 mg/mL chitosan/5 μM $A\beta_{40}$.[42] Furthermore, Doig and Derreumaux concluded in their extensive review of potential AD drugs that effective therapies against amyloid fibers should be done targeting small molecules.[40] Hence, this work is innovative because of the following: i) Polysaccharides from OFI are water-soluble, have a flexible backbone, and are amphiphilic in nature. They will be able to bind amyloid fibers in multiple points via electrostatic and hydrophobic forces. These intermolecular interactions will switch the hydrophobicity of Aβ segments, similar to how heavy crude oil molecules are dispersed; ii) Preliminary studies will show that low concentrations are effective to inhibit protein aggregation; iii) OFI is a plant with the largest amounts of glycans of various molecular weights to be able to select the compound(s) for optimal Aβ defibrillation, and iv) OFI is safe to ingest.

The search for new therapies to slow down the progression of AD in clinical trials has been challenging.[40] The premise is to inhibit the aggregation of the peptides that form AD plaques with natural polysaccharides from cactus. The research approach will focus on discerning the mechanism(s) that inhibit Aβ fibrillation and determining the trademarks that make polysaccharides successful to disperse or inhibit the formation of amyloid fibers.

Protein Aggregation Essay:

Aggregation and precipitation of normally-soluble proteins are the pathological hallmarks of several neurodegenerative diseases such as Parkinson's and Alzheimer's. Protein aggregates can be observed before the onset of disease symptoms in neurodegenerative diseases, and, therefore, protein aggregation is a relevant target for disease-modifying treatments. Preliminary experiments were performed with α-synuclein, which is an abundant 14 kDa protein. α-synuclein is intrinsically disordered under physiological conditions and is found primarily in neuronal tissue. α-synuclein aggregates are associated with Parkinson's disease.[47-49] The conversion of unfolded monomeric α-synuclein into the fibrillar state occurs through a complex process involving the formation of a partially-folded intermediate followed by the formation of an amyloidogenic nucleus and subsequent oligomerization and formation of protofibrils and fibrils.[49] During the fibrillation process, an increase in β-sheet content is observed, and the kinetics can be visualized in vitro by adding an amyloid fibril-sensitive dye such as thioflavin T (ThT).[50, 51] The fibrillation kinetics of α-synuclein are described by a sigmoidal curve containing a lag phase, an exponential phase, and a final plateau.[52] Two powders from the cactus were obtained by cutting, boiling, macerating, washing, and drying freshly harvested pads of OFI.[14, 16] One of the powders was collected from the solid portions that created a pulp (Extract S1); the other was separated from the liquid portions after maceration (Extract L1).

Figures 2, 3:
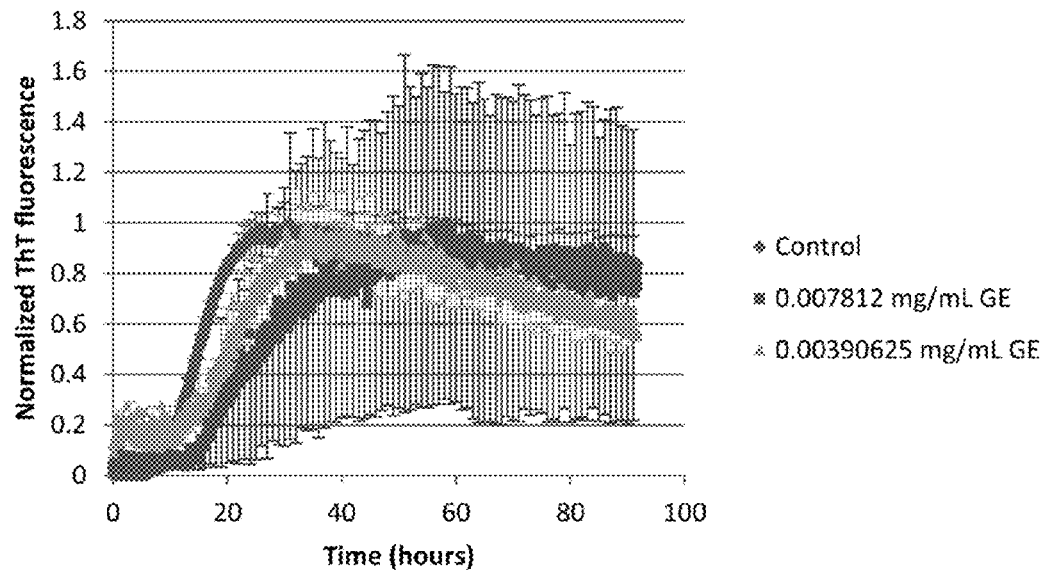
FIG. 2 is a graph depicting the effects of Extract S1 on aggregation kinetics of α-synuclein followed by ThT fluorescence at 37° C. in pH 7.4 phosphate buffer (50 mM Na-phosphate, 150 mM NaCl). Concentrations higher than 0.0078 mg/ml block protein aggregation and, therefore, do not show a lag-phase curve.
FIG. 3 is a table of concentrations and associated lag phases for extract S1.
Figure 4:
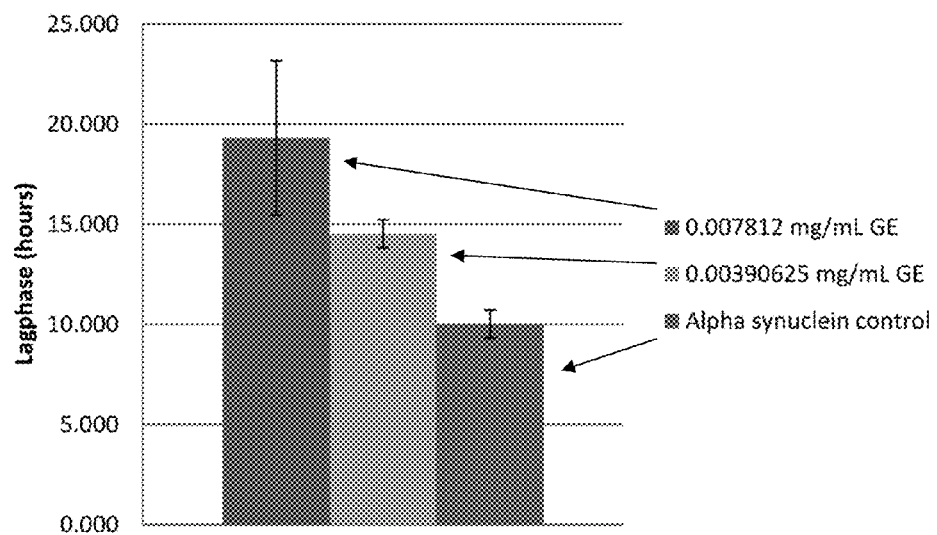
FIG. 4 is a graph depicting lag phase for different concentration of extract S1 versus an α-synuclein control.
Figure 5:
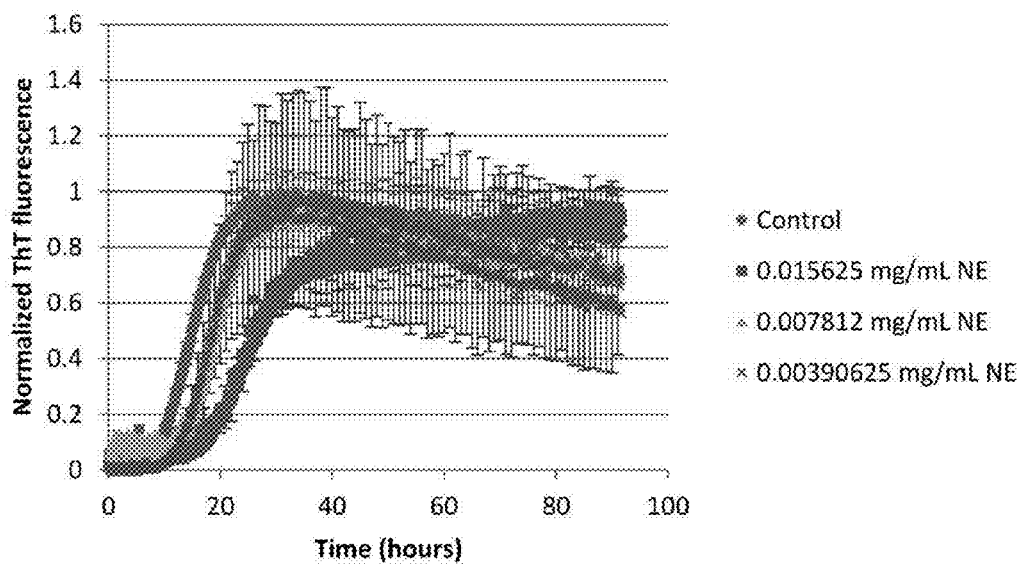
FIG. 5 is a graph depicting the effects of Extract L1 on aggregation kinetics of α-synuclein followed by ThT fluorescence at 37° C. in pH 7.4 phosphate buffer (50 mM Na-phosphate, 150 mM NaCl). Concentrations higher than 0.016 mg/ml block protein aggregation and, therefore, do not show a lag-phase curve.
Figures 6, 7:
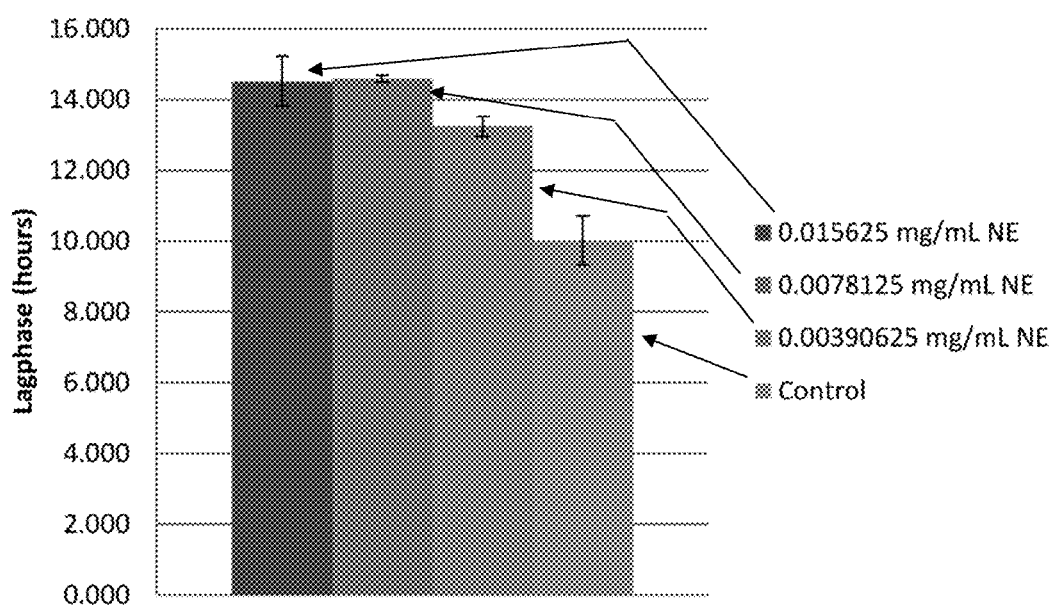
FIG. 6 is a table of concentrations and associated lag phases for extract L1.
FIG. 7 is a graph depicting lag phase for different concentrations of extract L1 versus an α-synuclein control.
Figure 8:
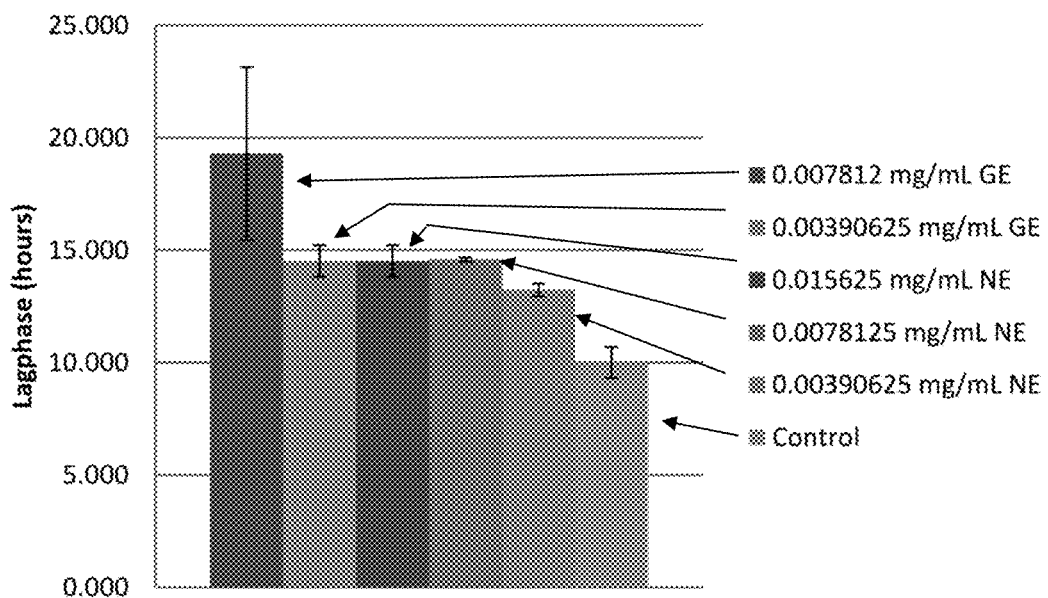
FIG. 8 is a graph depicting lag phase for the two extracts (S1 and L1) versus an α-synuclein control.
Figure 9:
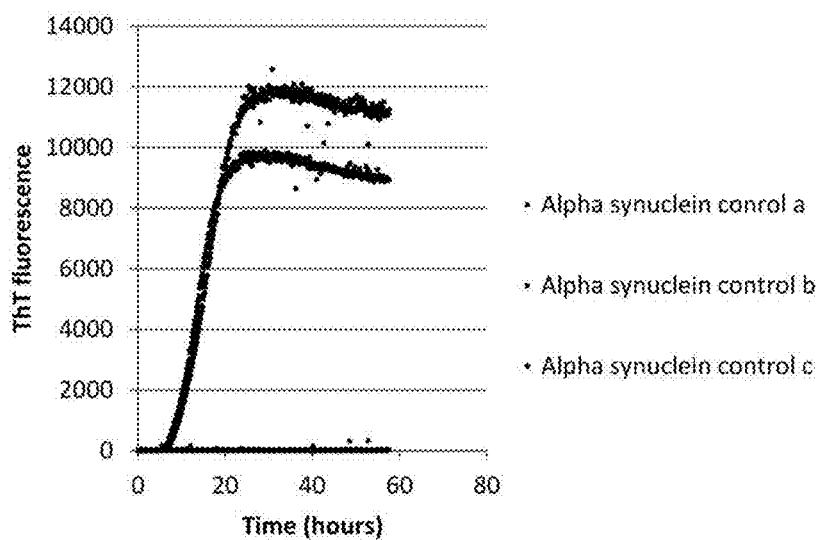
FIG. 9 is a graph depicting ThT fluorescence versus hours for α-synuclein controls a, b and c.
Figure 10:
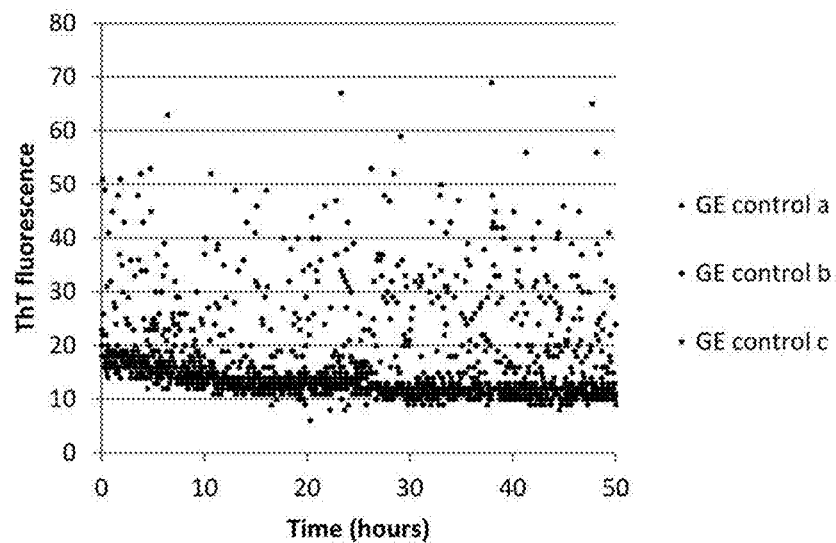
FIG. 10 is a graph depicting ThT fluorescence versus time for GE controls a, b and c.
Figure 11:
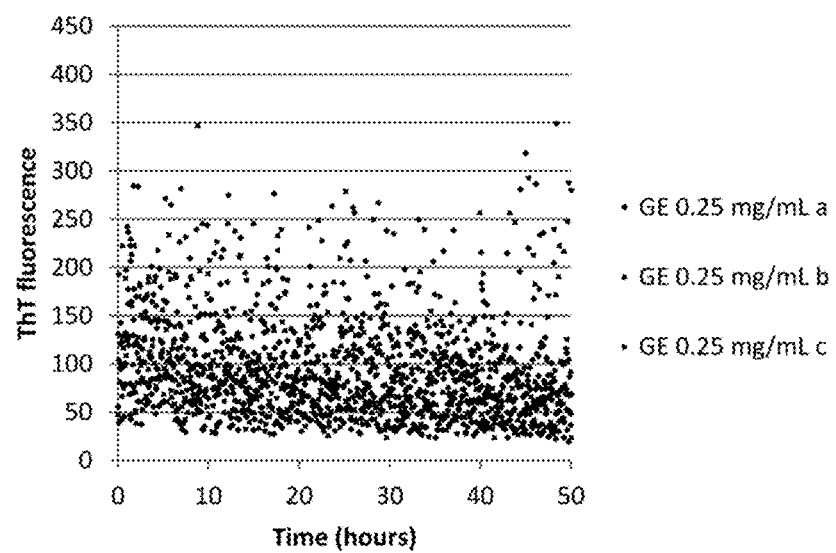
FIG. 11 is a graph depicting ThT fluorescence versus time for GE 0.25 mg/mL extracts a, b and c.
Figure 12:
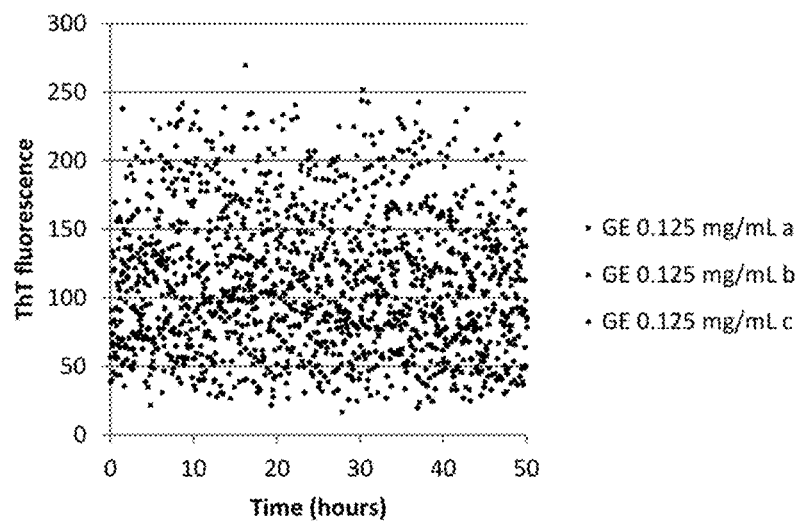
FIG. 12 is a graph depicting ThT fluorescence versus time for GE 0.125 mg/mL extracts a, b and c.
Figure 13:
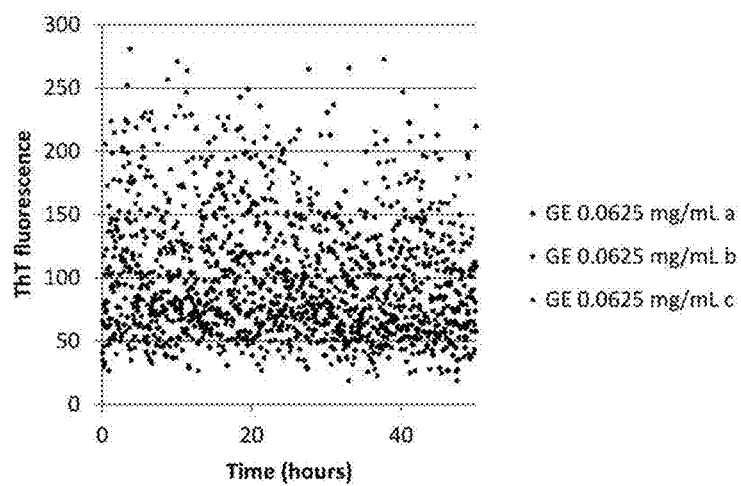
FIG. 13 is a graph depicting ThT fluorescence versus time for GE 0.0625 mg/mL extracts a, b and c.
Figure 14:
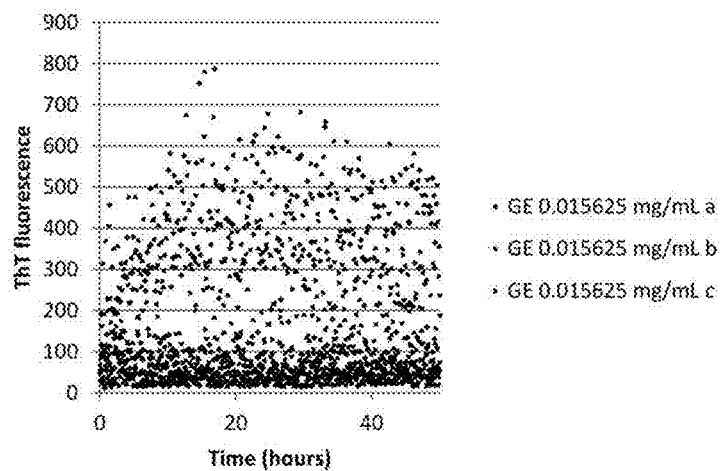
FIG. 14 is a graph depicting ThT fluorescence versus time for GE 0.015625 mg/mL extracts a, b and c.
Figure 15:
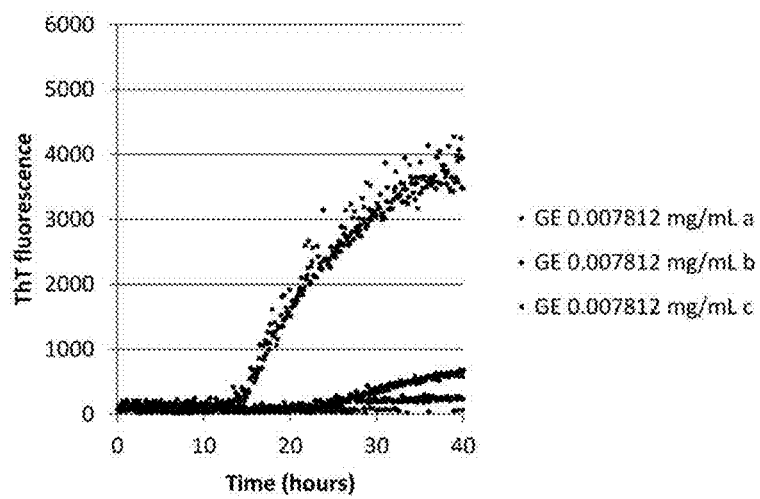
FIG. 15 is a graph depicting ThT fluorescence versus time for GE 0.007812 mg/mL extracts a, b and c.
Figure 16:
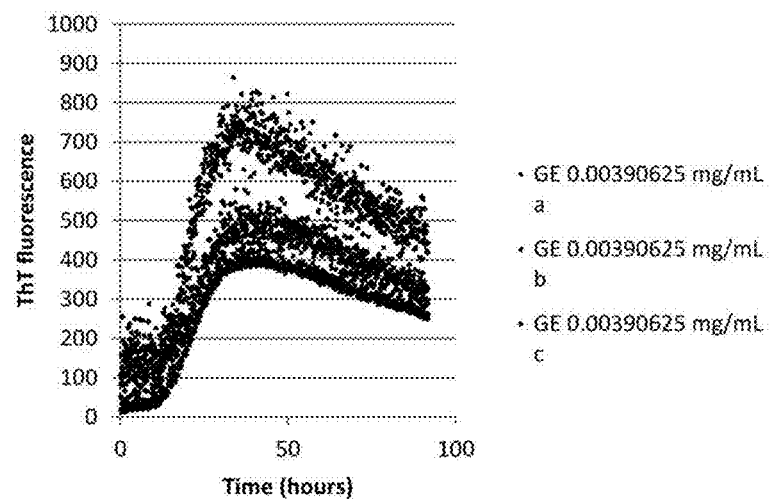
FIG. 16 is a graph depicting ThT fluorescence versus time for GE 0.00390625 mg/mL extracts a, b and c.
Figure 17:
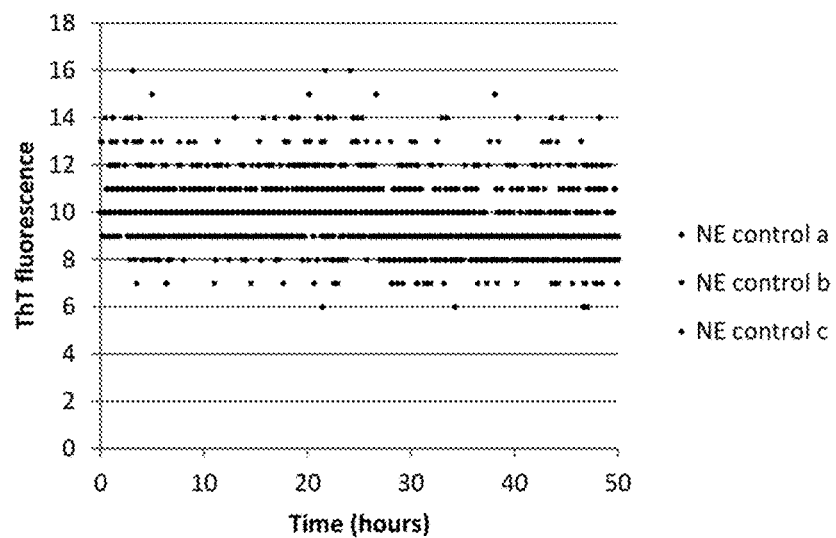
FIG. 17 is a graph depicting ThT fluorescence versus time for NE controls a, b and c.
Figure 18:
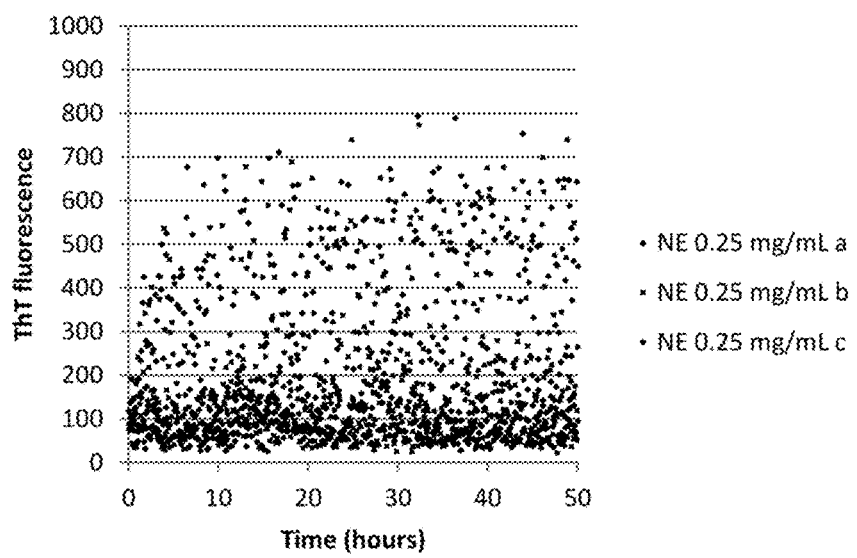
FIG. 18 is a graph depicting ThT fluorescence versus time for NE 0.25 mg/mL extracts a, b and c.
Figure 19:
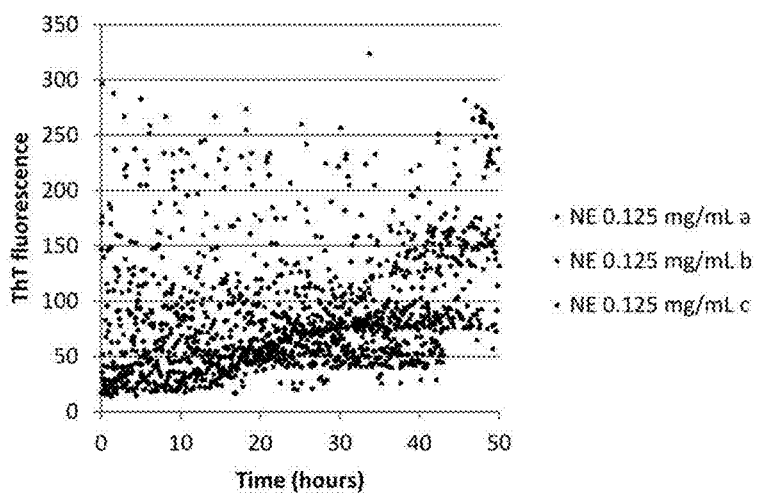
FIG. 19 is a graph depicting ThT fluorescence versus time for NE 0.125 mg/mL extracts a, b and c.
Figure 20:
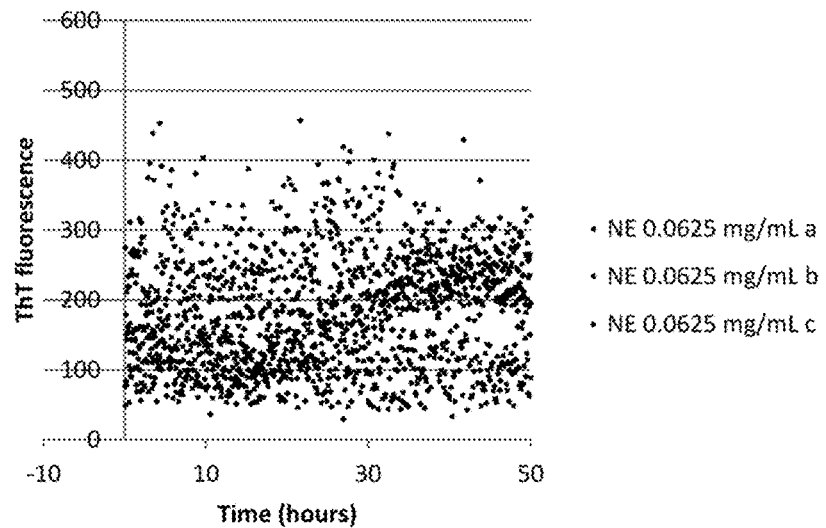
FIG. 20 is a graph depicting ThT fluorescence versus time for NE 0.0625 mg/mL extracts a, b and c.
Figure 21:
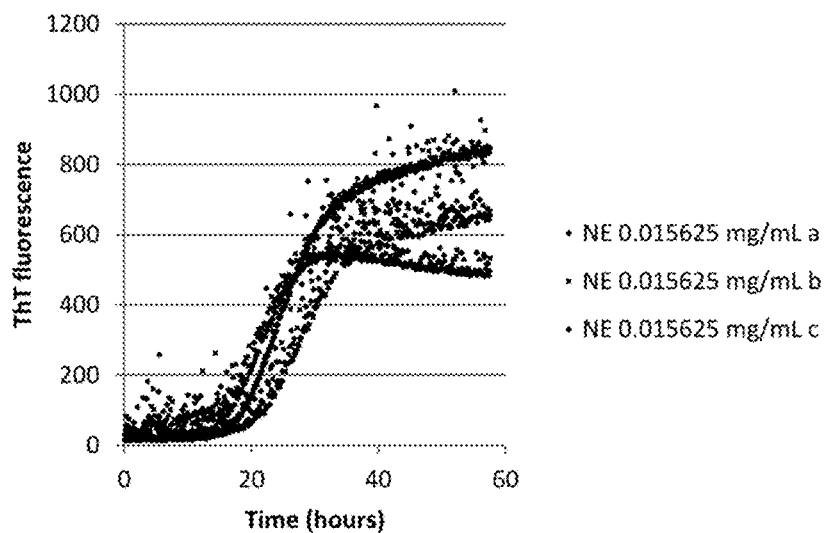
FIG. 21 is a graph depicting ThT fluorescence versus time for NE 0.015625 mg/mL extracts a, b and c.
Figure 22:
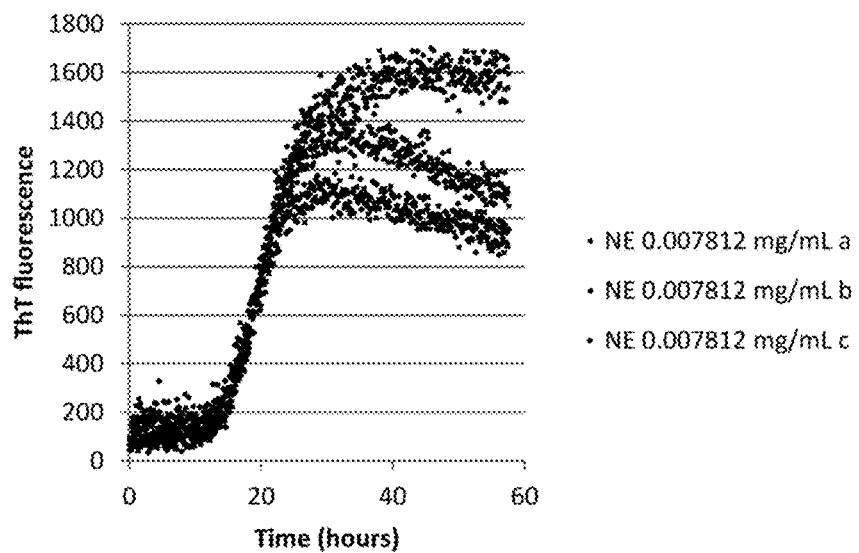
FIG. 22 is graph depicting ThT fluorescence versus time for NE 0.007812 mg/mL extracts a, b and c.
Figure 23:
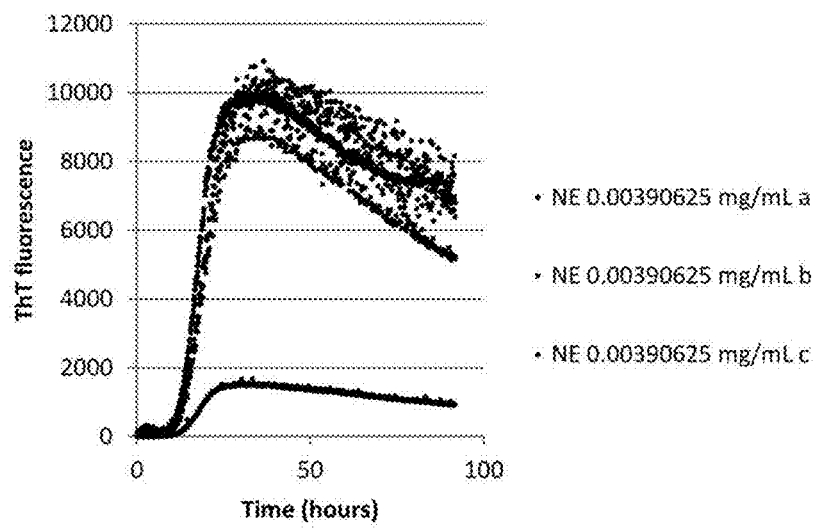
FIG. 23 is a graph depicting ThT fluorescence versus time for NE 0.00390625 mg/mL extracts a, b and c.
Figure 24:
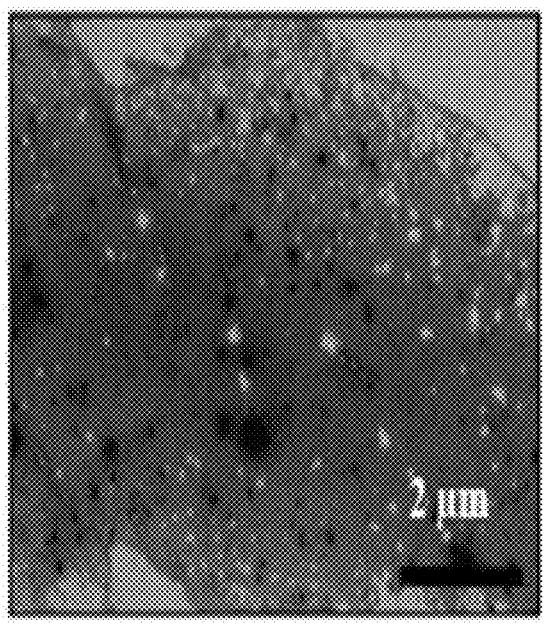
FIG. 24 is a TEM image depicting GE fraction 2 μm. Experimental analysis of ATR-FTIR spectra and the topology of the Aβ fibers indicate that the addition of cactus mucilage can modulate the kinetic formation of Aβ fibers.
Figure 25:
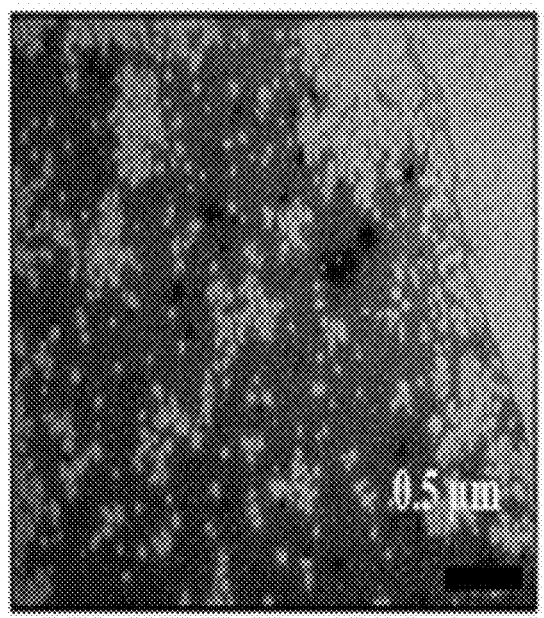
FIG. 25 is a TEM image depicting GE fraction at 0.5 μm. Experimental analysis of ATR-FTIR spectra and the topology of the Aβ fibers indicate that the addition of cactus mucilage can modulate the kinetic formation of Aβ fibers.
Figure 26:
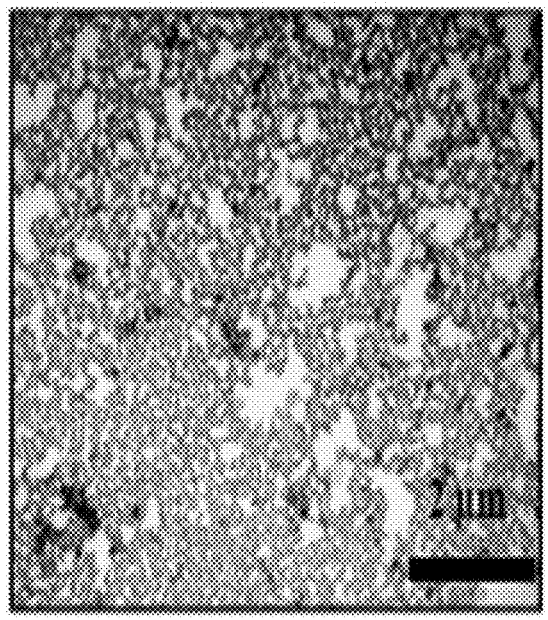
FIG. 26 is a TEM image depicting NE fraction at 2 μm. Experimental analysis of ATR-FTIR spectra and the topology of the Aβ fibers indicate that the addition of cactus mucilage can modulate the kinetic formation of Aβ fibers.
Figure 27:
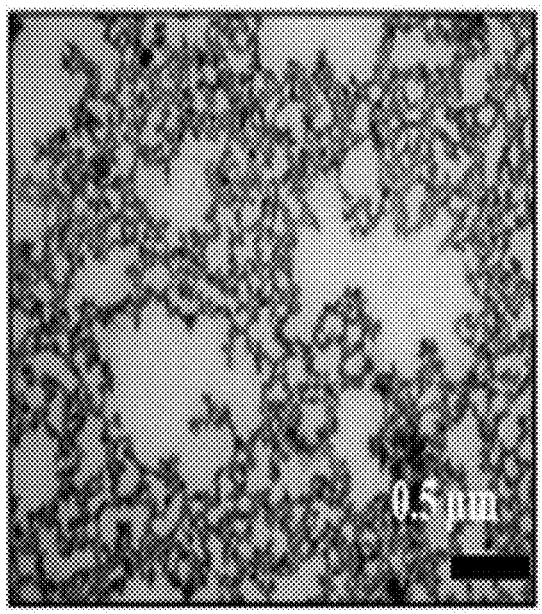
FIG. 27 is a TEM image depicting NE fraction at 0.5 μm. Experimental analysis of ATR-FTIR spectra and the topology of the Aβ fibers indicate that the addition of cactus mucilage can modulate the kinetic formation of Aβ fibers.
Figure 28:
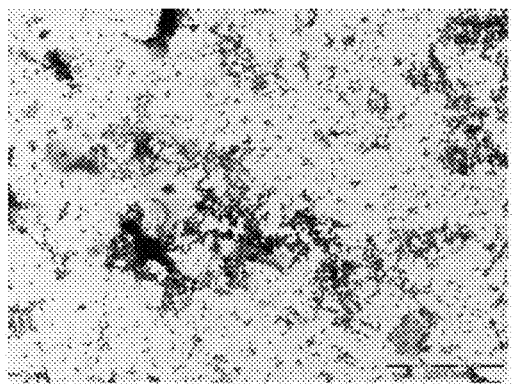
FIG. 28 is a TEM image of the aggregates obtained after 24 hours of incubation with cactus mucilage.
Figure 29:
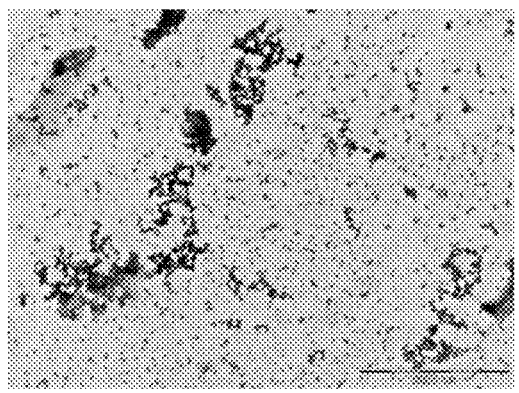
FIG. 29 is a TEM image of the aggregates obtained after 24 hours of incubation with cactus mucilage.

Both powders were then solubilized in 50 mM phosphate buffer (150 mM NaCl) at a pH=7.4 to create a stock solution of 0.5 mg/mL. Aliquots of individual extracts were added to solutions with the protein and ThT dye. The final concentrations of the protein and ThT were 0.25 mg/mL and 5 μM, respectively. FIGS. 2 and 5 show the lag-phase curves of the aggregation kinetics followed by ThT fluorescence for extracts S1 and L1. Although both extracts blocked protein aggregation at relatively low concentrations, the S1 extract completely blocked α-synuclein aggregation at approximately 1:20 mass ratios of extract/protein (Table 1). All experiments were repeated at least three times. Note that these results also show that depending on the way the natural extracts were obtained, they exhibited different functionalities. In this case, although L1 extract showed to be effective at mass ratios over 1:5 of extract/protein, S1 overperformed it. One advantage of using OFI is that its fractions are water-soluble, and it can be dissolved in solvents similar to the required phases for the protein aggregation essays. Another advantage is that once OFI is obtained in powder form, it can be stored and maintained dry at room temperature for future experimentation, with a shelf life greater than 6 years.[14, 16]

TABLE 1

Results of Protein Aggregation Assay (α-synuclein)

| Concentration (mg/mL) | Lag-phase Extract S1 [hrs] | Lag-phase Extract L1 [hrs] |
|---|---|---|
| OFI extract control 0.25 | No fibrillation | No fibrillation |
| α-synuclein control 0.25 | 10.0 ± 0.7 | 10.0 ± 0.7 |
| 0.25 | No fibrillation | No fibrillation |
| 0.125 | No fibrillation | No fibrillation |
| 0.0625 | No fibrillation | No fibrillation |
| 0.015625 | No fibrillation | 14.5 ± 1.2 |
| 0.007812 | 19.3 ± 3.9 | 14.6 ± 0.2 |
| 0.00390625 | 14.5 ± 0.7 | 13.2 ± 0.5 |

Although the preliminary data of the effect of OFI on protein aggregation were obtained using α-synuclein, other experiments for this research will track protein aggregation of Aβ peptides with 40 and 42 amino acids, either separately or combined. Comparing the response of α-synuclein vs. Aβ peptides will be valuable to understand the possible mechanism(s) of action for protein disaggregation.

Figure 30:
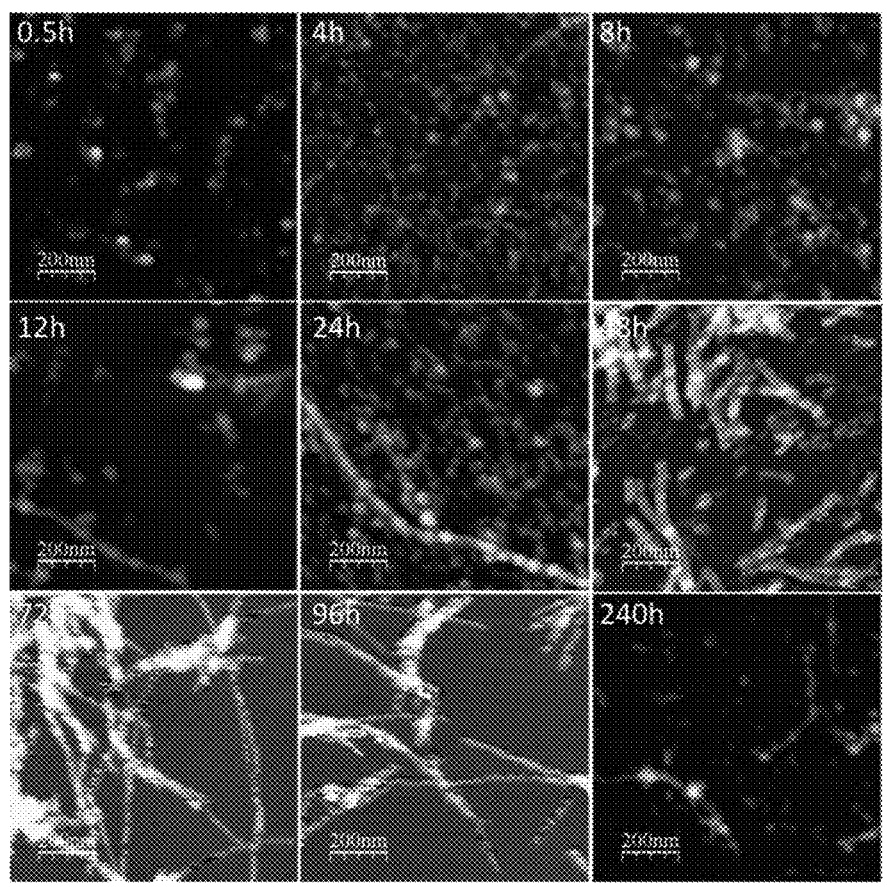
FIG. 30 is a series of images depicting the time evolution of $A\beta_{42}$ fibril growth by AFM following the described protocol. One can observe how amyloid fibrils are being formed as a function of incubation time. By 10 days (240 h), a mature plaque has been developed. Scan sizes are 2×2 μm from 0.5 to 96 h and 10×10 μm for the 240 h scan. The formation of fibrils is related to the transformation of antiparallel β-sheet structures of the peptide into parallel β-structures, as observed in FIG. 31. Scan height ranges from 0 to 15 nm.

Infrared (IR) Spectroscopy and Imaging Techniques:

IR spectroscopy allows one to recognize the structural chemistry of molecules under study in real time. AFM and SEM will be coupled to IR to monitor aggregate formation over time. The contact area of AFM probes is a function of the tip diameter and the topography of the surface where the tip is dragged. Height and features of the analyzed surface at the nanoscale are obtained directly.[53, 54] FIG. 30 shows topographic scans of the time evolution of $A\beta_{42}$ fibrils by AFM.

IR spectroscopy is being widely use for the analysis of peptides and proteins due to its reliability of probing the universally-available amide (peptide) bonds, which show distinct IR signals for differently folded peptides and proteins.[55-58] Proteins or polypeptides have a continuous chain of amino acids connected via amide bonds, also known as the "peptide bond." The frequency at which amide bond vibrations occur can be attributed to different secondary structures in which the amide bonds are present. One of the advantages of the ATR technique in recording protein spectra is the avoidance of solvent interference in IR spectra, because it limits the effective sample thickness to a thin layer near the surface of an internal reflection crystal.[59] The IR spectral resolution makes it possible to resolve the closely-spaced normal modes associated with molecular stretches. The sensitivity to both parallel and perpendicular components of the modes is the key to the mode assignment. Thus, structure determination and time resolution (~1 s) are compatible with kinetics taking place as concentration or temperature are varied.[55] Each infrared spectrum of the adsorbed peptide is obtained after subtraction of the spectrum of the vehicle solution containing all constituents (including polysaccharides) other than the peptide. Numerous references in the literature coincide in analyzing the IR region between 1500-1700 $cm^{-1}$ for protein quantification.[55, 60] Adsorbed proteins on surfaces unvaryingly present two regions that have been identified as Amide I and Amide II, as shown in FIG. 31a.

The integrated absorbance of the Amide I band (center at 1630 $cm^{-1}$) provides information on the secondary structure of the peptide (FIG. 31b). Each curve can be deconvoluted to correlate the presence of α-helical, anti-parallel, and parallel β-sheets; beta turns; and unordered structures, as shown in FIGS. 31b and 31c. The absorbance in the range of 1650-1658 $cm^{-1}$ is specifically associated with the presence of α-helix conformers, corresponding to the C=O stretch in primary amides. High- and low-frequency antiparallel β-sheets vibrations have been assigned to absorption bands centered at 1685 and 1610 cm$^{-1}$, respectively, which characterize the N—H vibration in Amide I. β-turns or simple turns have been shown to absorb near 1670 cm$^{-1}$. Parallel β-sheets are known to peak at 1625 cm$^{-1}$ (FIG. 31b). The critical variables that determine the chemical and structural conformation of Aβ entities are incubation time, solvent, solution concentration, temperature, pH, ionic strength, and Aβ sequence.[61, 62] The inventors have based our protocols to prepared fibrillar aggregates of Aβ$_{40}$ & Aβ$_{42}$ peptides in previously-published work.[62-65] FIG. 31d shows the secondary structure content, which is calculated taking the peak positions from the second derivative of the spectrum per each time. Both FIGS. 31c and 31d are congruent. IR spectra of OFI and AFM scans of its nano-structure have been published by the PI's group and could not be shown in this proposal due to space limitations.[7, 14, 16]

The results indicate that natural polysaccharides from OFI induce an effect to block the fibrillation of amyloid beta fibers. The inventors also have shown that the secondary structure of these fibers can be followed in real time with ATR-FTIR and that fibrillation is dominated by parallel β-sheet conformations. However, the inventors do not have information on how the molecularly-kinetic mechanisms of the fibrillation process are impacted by natural polysaccharides or the important features that polysaccharides exhibit by being in contact with amyloid beta or α-synuclein. The inventors also noticed that depending on the fraction of OFI, the effects can be quite different. It is not known if one or many glycans contribute to the defribrillation process.

Identify the Conditions at Which Polysaccharides from Cactus Extracts can Destabilize Amyloid Fiber Formation.

Polysaccharide intermolecular interactions with Aβ peptides will lead to block fibrillation promoting AD plaques dispersions.

The natural cactus contains polysaccharides that have shown to access heavy molecules with a large number of hydrophobic groups via surface interfacial properties, which create stable emulsions in aqueous environments. The plant contains polysaccharide fractions that are in charge of water storage. Other polysaccharides are involved in moving nutrients to support the plant through extreme climate conditions due to hot and cold temperature gradients in short periods of time, as it occurs in arid areas where these cacti are known to flourish. Hence, depending on the extraction process, different fractions can be obtained. The molecular conformations of fibrillar deposits displaying a high content of parallel β sheets will undergo conformational changes due to the presence of polysaccharides. Such interactions will be monitored and recorded to elucidate the mechanism(s) of action for protein disaggregation. The inventors expect to determine i) if these interactions change parallel β sheets to antiparallel β strands, ii) if polysaccharide binding can be strong enough to cleave the fibrils out of a plaque formation, and iii) what interactions disrupt the kinetic mechanisms of fibril formation.

Experimental Approach:

In both protein aggregation and ATR-FTIR experiments, the inventors will examine the effects of adding OFI polysaccharides at the beginning of the incubation or after fibers are formed. The inventors will compare three ways of separating polysaccharides from OFI: gelling extracts (GE), non-gelling extracts (NE), and combined (both GE and NE). Control solutions will consist of the materials by themselves. The Aβ material will be $Aβ_{42}$, $Aβ_{40}$, or mixtures of $Aβ_{40}$:$Aβ_{42}$ (at 50:50, 70:30, or 90:10 ratios). For each condition of Aβ or α-synuclein, the inventors will test eight concentrations of OFI extracts at mass ratios of 0 (no extract), 1:5, 1:10, 1:15, 1:20, 1:30, 1:50, and 1:100. The inventors will perform a time-course analysis of these incubations, drawing samples at 0.5, 1, 2, 4, 8, 12, 24, 36, 48, 72, and 120 hours of incubation. These samples will be analyzed for aggregation by AFM and for conformation by ATR-FTIR. The studies will be repeated at least three times to corroborate reproducibility of the measurements. Simultaneously, the same conditions will be monitored with ATR-FTIR in situ. The following specific methods for each experiment will be performed.

Protein Aggregation Studies:

Conditions for protein aggregation will be optimized for each protein. Aggregation of α-synuclein (0.25 mg/ml) will be conducted in a 20 mM Tris buffer, pH 7.5 in the presence of 5 μM heparin at 37° C. Aggregation of the Aβ (both 40 and 42) peptide (0.07 mg/ml) will be conducted in a 20 mM Tris buffer, pH 7.5 at 30° C. Protein will be initially dissolved in 1 mM NaOH at 4 mg/ml, incubated in this solution for 1 min, and diluted into the final reaction buffer. Protein aggregation in the presence of extracts will be carried out in a reaction volume of 0.1 ml in black, flat-bottomed, 96-well plates in the presence of 5 μM ThT. Two Teflon balls (2.38 mm diameter, Precision Ball, Reno, Pa.) will be placed into each well of a 96-well plate. The reaction mixture containing protein and ThT (320 μl) will be split into three wells (100 μl into each well), and the plates will be covered with Mylar septum sheets (Thermo) and incubated with continuous orbital shaking at 280 rpm in an Infinite M200 Pro microplate reader (Tecan). The kinetics will be monitored by top reading of fluorescence intensity every 3-5 minutes at 444 nm excitation and 482 nm emission. Data from replicate wells will be averaged. The data will be fit to a sigmoidal equation using SigmaPlot (Systat, San Jose, Calif.). The equation is $F=A+B/(1+\exp(k\times(t-t_m)))$ (Eq. 1), where A is the initial level of ThT fluorescence, B is the difference between the final level of ThT fluorescence and its initial level, k is the rate constant of amyloid accumulation ($h^{-1}$), and $t_m$ is the midpoint of transition. The lag time ($t_1$) of amyloid formation was calculated as $t_1=t_m-2/k$. The parameters derived from this equation are yield of amyloid (B), lag time ($t_1$), and elongation rate (k) of amyloid. Initiation rate is defined as the inverse of lag time. Although Eq. 1 gave good fit for the ThT kinetic profiles, the expression is strictly an empirical means of deriving kinetic parameters from the data and does not necessarily reflect the underlying complex kinetic scheme.

OFI extracts derived from the macerated solids of the plant are pectin-rich polysaccharides also called gelling extracts (GE). Extracts from the liquids after separating the macerated solids provides an Arabinose-rich extract termed non-gelling (NE). Both GE and NE form a combined fraction. Details on extracting the fractions can be found in the patented protocol for the PI's group.[66]

The optimal concentration of cactus extracts necessary to induce disorder in Aβ fibrils will be determined by two independent techniques. ATR-FTIR will decipher molecular information on the kinetic disruption mechanisms of fiber formation and, ultimately, on the fate of AD plaques due to the addition of polysaccharides. By knowing the optimal conditions and dosage of cactus extracts that effectively disrupt Aβ fibers, it will lead us to determine what glycan components have a specific interaction with individual Aβ amino acids. Information from this aim will be valuable for the later design of targeting therapies that can slow down the progression of AD using natural polysaccharides.

Separate and Characterize the Polysaccharides Responsible for AD Fibrils Disruption.

Natural OFI extracts are a mixture of many different polysaccharides. However, results from Aim 1 will narrow the pool and allow us to discern what kind of specific compound(s) from OFI extracts effectively block fibrillation.

By determining size, functionality, and chemical composition of subfractions from successful individual extract concentrations, the inventors will be able to elucidate its structure. This will lead us to work on the potential development for safe drugs that are effective against neuronal death caused by amyloid plaques.

GPC chromatograms to be obtained for both extracts likely will have multiple peaks at various retention times. This means that both extracts comprised multiple fractions with different molecular weight distributions. Major peaks in what are considerably smaller retention times and compared to those from standard sugar samples with similar structure and functionality will mean that the extracts mainly comprise large molecules. Interestingly, if GE and NE chromatograms show peaks at retention times greater than the standards for small-size polysaccharides, this can be attributed to very small molecules. Using HPLC as a separation technique, the extracts can be fractionated into two different portions with significant size differences and functionality for the three OFI extracts and its subfractions. Once the compounds are compared to pure synthetic sugars, the inventors will be able to determine their precise structure. However, in the event that the exact sugar is not commercially available, the inventors will use synthetic methods to build up blocks of sugars to replicate the natural fraction that was detected by the analytical techniques. The protocols for physical characterization are as follows.

The molecular weight distribution of the purified polysaccharide can be determined using an Agilent GPC system equipped with a water-based gel column and, coupled with a differential refractometer, will be used to determine the molecular weight distribution. Standard pullulan polysaccharide calibration kits (10-15 different molecular weights: 180, 667, 1000, 5000, 10000, 20000, 50000, 100000, 200000, 300000, 400000, 700000, 900000, 1000000 g/mol) will be passed through the column to obtain the calibration curve, which will then be used to determine the molecular weight.

The carbohydrate composition of the GE and NE extracts will be performed using the NREL LAP protocol "Determination of Structural Carbohydrates and Lignin in Biomass" (NREL 2008).[67-69] The soluble sugars will be quantified by HPLC equipped with a refractive index detector. Briefly, OFI extracts will be added to 2 ml of 0.005 M sulfuric acid (HPLC mobile phase). To get the equation of calibration curve, a series of calibration standards (xylose, cellulose, galactose, arabinose, glucose, sucrose, and mannose) will be prepared and injected into the system. The structure of the fractions will be compared with those from the standards to identify the matching glycan function. The following chromatographic conditions will be used: Biorad Aminex HPX-87H column at 55-65° C., mobile phase (0.005 M sulfuric acid; rate 0.6 mL/minute), RI detector, injection volume range from 1-125 µL.

Aldolase-Catalyzed Condensation reactions will be followed to construct specific polysaccharides scaling from 0.01 to 1 mol to mimic the properties of those from the OFI extracts.[70-72] In this method, aldolase enzyme (from rabbit muscle) along with dihydroxyacetone phosphate (DHAP) as one substrate, will be exposed to judicious compositions of myriad aldehydes molecules to be able to reconstruct glycan using block-by-block assembly until the desired structure is achieved. The advantage for using this type of reactions is that the inventors will be able to control stereochemistry for each sugar block.[70]

Knowing size and structural functionality of natural polysaccharides, which the inventors expect will be able to inhibit protein aggregation, will provide insights on how to optimize further amyloid interactions to maximize its effectiveness. Since the molecular weight of specific extracts and subfractions of OFI will be determined, the inventors will be able to correlate molar percentages to the computation of effective concentrations, allowing us to discern the conformational changes that polysaccharides induce on the $A\beta$ peptides and correlate such info with the structure and type of interaction from polysaccharide-A $\beta$ binding sites. The inventors will be able to determine effective stoichiometry molar ratios of polysaccharides with respect to amyloid aggregates. The ultimate outcome will be to identify the extent to which glycans can modify $A\beta$ secondary structure and determine the impact of this mechanism in relation to other mechanisms in mouse models and patients for future applications to prevent AD plaques.

Statistical Analysis

Each essay and analytical measurement as well as analysis from the ATR-FTIR experiments will be done in triplicate. Comparisons among OFI extract concentrations will be made at specific time points (those after IR signals indicate aggregate Example Polymer Extraction and Characterization Pectin-based polysaccharide was extracted from the *Opuntia ficus-indica* (OFI) cactus using an alkaline extraction medium. Two different fractions were isolated from the cactus pads. Gelling extract (GE) and non-gelling extract (NE). Fully de-esterified extracts demonstrated excellent gelling properties in the presence of $Ca^{2+}$ ions. The amount of uronic acid was calculated using potentiometric titration. The extracts were characterized using Attenuated Total Reflection-Fourier Transform Infrared Spectroscopy (ATR-FTIR) and gel permeation chromatography (GPC). GPC showed the polysaccharide to be composed of at least three main fractions with various molecular weights. The Extracts contain a myriad of high, medium, and low molecular weight polysaccharides. The ATR-FTIR spectra of extracts showed the characteristics of pectin based polysaccharides with high content of uronic acid. Transmission Electron Microscopy (TEM) was used to observe the morphology of the extracts.

Surface-Tethered Cross-Linked Thin Films

A protocol for fabricating surface-tethered cross-linked thin films of pectin based polysaccharide was developed. Thin films were synthesized using both extracted polysaccharide from OFI and commercially available high molecular weight pectin. Surface attached thin films were fabricated by spin coating the solution of pectin based polymers on a substrate. The thin films were cross-linked by introducing $Ca^+$ ions. The pectin films were successfully fabricated at various thicknesses ranging from 50 nm up to sub-microns. Thin films were then cross-linked using $CaCl_2$ at various concentrations to obtain cross-linked thin films with different cross link densities. By using surface-anchored linkers, thin polymer layers was immobilized to various solid substrates while the cross-link density and thickness was independently controlled through simply varying the concentration of the polymer solutions and Ca$^+$ ions. The resultant cross-linked thin films were characterized using ellipsometry to evaluate the thickness of the films. The cross-linked films were then exposed to water to measure the equilibrium water intake and volume-phase transition temperature. The volume phase transitions of the coatings were studied under the influence of temperature and ion concentrations. The changes in the molecular environment during the transition were also investigated by ATR-FTIR.

Bulk Gel Fabrication

To better understand the impact of confinement on the phase transition behavior of a polymer network, bulk gels were also prepared from both extracted polysaccharide from OFI and commercially available pectin. The gelling behavior of this material was studied as a function of amount of Ca$^{2+}$ added and temperature. Addition of Ca$^{2+}$ was adjusted at varying stoichiometric ratios of $[Ca^{2+}]/[COO^-]$). The hydrogels with various cross-link densities were prepared and freeze dried to calculate the dry weight. Dry gels were then immersed into the water to measure the water intake capacity. Swelling ratio of the hydrogels was measured as a function of temperature of the medium. For the temperature measurement, the hydrogels were soaked in solutions of different temperatures ranging from 15° C. to 70° C. for 24 h. The equilibrium swelling ratio of the hydrogels was determined afterwards.

Counteracting the Formation of Amyloid Plaques by Natural Polysaccharides

Aggregation of amyloid proteins into plaques that cause neural death is associated with neurodegenerative diseases. Alterations of the aggregation pathways of amyloid peptides to produce less toxic structures or to disrupt the formation of fibrils are a promising therapeutic approach. The inventors have studied the ability of the extract from the OFI cactus to disrupt Aβ and α-Synuclein fibril formation. The inventors have looked at the aggregation kinetics of amyloid peptides in the presence of different concentrations of the novel cactus extracts. The extracts from the solid parts (i.e., gelling extracts, GE), non-gelling extracts (NE) from the liquid fractions, or combined extracts (both GE and NE) were separated from the fresh pads. The effect of both GE and NE extracts to disrupt the aggregation formation was studied. Moreover, these extracts contain at least three different fractions as it was observed by GPC; myriad high, medium, and low molecular weight polysaccharides. Three main fractions were isolated from the extracts to evaluate their ability to disrupt the aggregation individually. In order to deeply examine the mechanism of protein aggregation in presence of cactus mucilage extract, two set of experiments were performed. First, the effect of mucilage addition to prevent protein aggregation was studied. Moreover, in order to assess the interaction of mucilage with preformed mature fibrils, mucilage solutions were added to mature aggregated proteins. This enabled us to separately study both the disruptive and inhibitory effects of mucilage extracts.

The conditions at which polysaccharides from cactus extracts can destabilize amyloid beta fiber formation were identified using a Thioflavin T (ThT) fluorescence aggregation assay. Using the ThT assay, the optimal concentration of cactus extracts that can disperse amyloid aggregates was identified. Protein aggregation was carried out in a reaction volume of 0.1 ml in flat-bottomed 96-well plates in the presence of 5 μM ThT. The kinetics was monitored by top reading of fluorescence intensity as a function of the incubation time. The measured intensities were reported as a function of time using a sigmoidal curve comprised of three main parts: a lag-phase, an exponential phase and a final plateau. The obtained results showed that mucilage solution can disturb the protein aggregation kinetics significantly. Our results showed that the lag phase of amyloid fibril formation was significantly increased. Moreover, it was observed that the GE extract completely inhibited the amyloid fibril formation process at mass ratios of 1:20 extract/protein. NE extract also blocked the aggregation at ~1:10 mass ratios of extract/protein. Both extracts blocked the protein aggregation at relatively low concentrations. These represent much lower ratios than found with other natural inhibitors. Below these critical ratios, aggregation kinetics were dependent on the extract concentrations.

The kinetics were also monitored with ATR-FTIR spectroscopy and TEM. Using ATR-FTIR, the inventors have looked at the kinetic disruption mechanisms of the plaques due to the addition of cactus extracts. Infrared (IR) Spectroscopy allows one to recognize the structural chemistry of molecules under study in real time. The amide bands (amide I and amide II regions) reveals the changes happen to the backbone of the peptide. The amide I region can be studied by its deconvolution into different peaks. Each of these peaks correspond to an existing secondary structure of the peptide. Therefore, it is possible to monitor the secondary structure of the amyloid proteins during the aggregation processes studied. Using ATR-FTIR, the inventors were able to elucidate the molecular interactions between amyloid peptide species and mucilage extracts. The inventors have looked at the disruptive effect of mucilage extracts on preformed Aβ fibrils. Both extracts were added to the mature fibers at relatively low concentrations starting from 1:1 down to 1:100 mass ratios of extract/protein. The interaction of the extracts and fibrils were monitored over 12 hours. All recorded spectra were deconvoluted to monitor n-sheets content. Our data showed that both extract are able to destabilize amyloid fibers at approximately 1:4 mass ratios of extract/protein. In general, the inhibitory effect of mucilage extracts to target Amyloid proteins appears to be more effective than targeting fully formed fibrils.

Cell Viability Assay

The cytotoxicity of both GE and NE extract was examined by the MTT assay using NIH3T3 cells. Both extracts found to be non-toxic at the concentration ranging from 0.5 mg/ml down to 0.001 mg/ml.

Brain Cell Targeting for Specific Targeting and Disease Treatment

Attenuated Total Reflectance-Fourier Transform Infra-Red (ATR-FTIR) Spectroscopy was used to investigate the possible molecular interaction between chlorotoxin and model brain cells. The incorporation of chlorotoxin in this system has been achieved and evaluated. Chlorotoxin, a 36-amino acid peptide, is purified from Leiurus quinquestriatus scorpion venom with a distinct characteristic of binding preferentially to neuroectoderma tumors such as glioma, but not to normal tissue. This study presents a new approach in monitoring the biochemical and biophysical changes in targeting systems for inducing localized therapeutics in the brain. In addition to characterizing the signature spectra of CTX and normal and glioma cells, the inventors evaluated the differences in biochemical compositions of the spectra of the model brain cells treated with and without CTX over different incubation time periods.

REFERENCES

1. Nobel, P. S., *Cacti: Biology and Uses.* 2002, Berkeley: University of California Press.
2. Bennett, Z. W. A., Topical composition used for treating body and skin disorder, comprises Aloe vera, shea butter, cocoa butter and/or cactus plants, alcohol, Opuntia aqueous extract, cherry or coconut flavoring, essential oil, vitamin D, and vitamin E: Assignee: Bennett Z W A.
3. El-Mostafa, K., El Kharrassi, Y., Badreddine, A., Andreoletti, P., Vamecq, J., El Kebbaj, M. S., Latruffe, N., Lizard, G., Nasser, B. and Cherkaoui-Malki, M., *Nopal Cactus (Opuntia ficus-indica) as a Source of Bioactive Compounds for Nutrition, Health and Disease.* Molecules, 2014. 19(9): p. 14879-p 14901.
4. Moran-Ramos, S., Avila-Nava, A., Tovar, A. R., Pedraza-Chaverri, J., Lopez-Romero, P. and Torres, N., *Opuntia ficus indica (nopal) attenuates hepatic steatosis and oxidative stress in obese Zucker (fa/fa) rats.* The Journal of Nutrition, 2012(11): p. 1956.
5. Sinnott, M., Carbohydrate Chemistry and Biochemistry: Structure and Mechanism. 2007, Cambridge, UK: RSC Publishing.
6. U.S. National Library of Medicine, DailyMED. NIH-NLM 2016; Available from: http://dailymed.nlm.nih.gov/dailymed/search.cfm?labeltype=all&query=opuntia.
7. Fox, D. I., Stebbins, Daniela M., and Alcantar, Norma A., *Combining Ferric Salt and Cactus Mucilage for Arsenic Removal from Water.* Environ. Sci. Technol., 2016: p. DOI: 10.1021/acs.est.5b04145.
8. Costa, R. G., Trevino, I. H., de Medeiros, G. R., Medeiros, A. N., Pinto, T. F. and de Oliveira, R. L., *Effects of replacing corn with cactus pear (Opuntia ficus indica Mill) on the performance of Santa Ines lambs.* Small Ruminant Research, 2012. 102(1): p. 13-17.
9. Mahouachi, M., Atti, N. and Hajji, H., Use of Spineless Cactus (*Opuntia ficus indica* f. inermis) for Dairy Goats and Growing Kids: Impacts on Milk Production, Kid's Growth, and Meat Quality. Scientific World Journal, 2012.
10. Ortiz-Rodriguez, R., Valdez-Alarcon, J. J., Gomez-Ramos, B., Lopez-Medina, J., Chavez-Moctezuma, M. P., Garcia-Saucedo, P. A. and Perez-Sanchez, R. E., *Yield and microbiological quality of raw milk and fresh cheese obtained from holstein cows receiving a diet supplemented with nopal (Opuntia ficus-indica).* African Journal of Microbiology Research, 2012. 6(14): p. 3409-3414.
11. Jenny Ross, Healing with Raw Foods: Your Guide to Unlocking Vibrant Health Through Living Cuisine. 2014, New York, N.Y.: Hay House, Inc.
12. Carolyn J. Niethammer, R. S., *The Prickly Pear Cookbook.* 2004: Rio Nuevo Publishers.
13. Buttice, A. L. and Alcantar, N., Sediment Removal with the *Opuntia ficus-indica* Cactus: A Water Purification Method for Communities in Latin America, in Comprehensive Water Quality and Purification, in Comprehensive Water Quality and Purification, S. Ahuja, Editor. 2013, Elsevier: New York.
14. Buttice, A. L., Stroot, J. M., Lim, D. V., Stroot, P. G. and Alcantar, N. A., *Removal of Sediment and Bacteria from Water Using Green Chemistry.* Environmental Science & Technology, 2010. 44(9): p. 3514-3519.
15. Pichler, T., Young, K. and Alcantar, N., *Eliminating turbidity in drinking water using the mucilage of a common cactus.* Water Science & Technology: Water Supply, 2012. 12(2): p. 179-186.
16. Fox, D. I., Pichler, T., Yeh, D. H. and Alcantar, N., *Removing Heavy Metals in Water: The Interaction of Cactus Mucilage and Arsenate (As (V)).* Environmental Science & Technology, 2012. 46(8): p. 4553-4559.
17. Leon, J., (Major Professor, Alcantar, Norma), Thesis: *Opuntia ficus-indica Mucilage Potential to Remove Nuclear Active Contaminants From Water Based on a Surrogate Approach.* Chemical & Biomedical Engineering, USF. Vol. Graduate Theses and Dissertations. htt:// scholarcommons.usf.edu/etd/5253. 2014, Tampa: University of South Florida.
18. Stebbins, D., Buttice, A. L., Fox, D., Smith, D. M. and Alcantar, N., Cactus Mucilage as an Emergency Response Biomaterial to Provide Clean Drinking Water, in Monitoring Water Quality: Pollution Assessment, Analysis, and Remediation, S. Ahuj a, Editor. 2012, Elsevier: New York. p. 249-260.
19. Agyare, C., Boakye, Y. D., Bekoe, E. O., Hensel, A., Dapaah, S. O. and Appiah, T., *Review: African medicinal plants with wound healing properties.* Journal of Ethnopharmacology, 2016. 177: p. 85-100.
20. Antunes-Ricardo, M., Gutierrez-Uribe, J. A., Lopez-Pacheco, F., Alvarez, M. M. and Serna-Saldivar, S. O., *In vivo anti-inflammatory effects of isorhamnetin glycosides isolated from Opuntia ficus-indica (L.) Mill cladodes.* Industrial Crops and Products, 2015. 76: p. 803-808.
21. Cota-Sanchez, H., Taxonomy, distribution, rarity status and uses of Canadian Cacti. Haseltonia, 2002. 9: p. 17-25.
22. Radia Lamghari El Kossori, C. V., Essadiq El Boustani, Yves Sauvaire, Luc Mejean, *Composition of pulp, skin and seeds of prickly pears fruit (Opuntia ficus indica sp.).* Plant Foods for Human Nutrition, 1998. 52: p. 263-270.
23. Techtenberc, S. and Mayer, A. M., *Composition and properties of opuntia ficus-indica mucilage.* Phytochemistry, 1981. 20(12): p. 2665-2668.
24. Alcantar, N., A., Fox Dawn I.; Thomas, Sylvia, W.; and Toomey, Ryan, G., *Use of Cactus Mucilage as a Dispersant and Absorbant for Oil in Oil-Water Mixtures.* 2015, U.S. Pat. No. 9,163,374. Assignee: University of South Florida.
25. Gateau, P., Henaut, I., Barre, L. and Argillier, J. F., *Heavy oil dilution.* Oil & Gas Science and Technology-Revue D Ifp Energies Nouvelles, 2004. 59(5): p. 503-509.
26. Norma A. Alcantar, D., Fox, Sylvia Thomas, Ryan G. Toomey, *Use of cactus mucilage as a dispersant and absorbant for oil in oil-water mixtures* U.S. Pat. No. 9,163,374B2. 2015: University of South Florida.
27. Stebbins, D., Buttice, A. L., Fox, D., Smith, D. M. and Alcantar, N. A., *Cactus Mucilage as an Emergency Response Biomaterial to Provide Clean Drinking Water.* Monitoring Water Quality: Pollution Assessment, Analysis, and Remediation, 2013: p. 249-260.
28. Holm, E. K., ed. *Dispersants in Oil Spills.* ed. E.a.T. Environmental Science. 2011, Nova Science Publishers: New York.
29. El Kossori, R. L., Villaume, C., El Boustani, E., Sauvaire, Y. and Mejean, L., *Composition of pulp, skin and seeds of prickly pears fruit (Opuntia ficus indica sp.).* Plant Foods for Human Nutrition (Dordrecht), 1998. 52(3): p. 263-270.
30. El Kossori, R. L., Villaume, C., El Boustani, E.-S., Sauvaire, Y. and Mejean, L., *Composition and nutritional prospects of prickly pear fruit.* Proceedings of the Nutrition Society, 1999. 58(3): p. 87A-87A.
31. Uversky, V. N., Functional roles of transiently and intrinsically disordered regions within proteins. Febs Journal, 2015. 282(7): p. 1182-1189.

32. Sluchanko, N. N. and Uversky, V. N., Hidden disorder propensity of the N-terminal segment of universal adapter protein 14-3-3 is manifested in its monomeric form: Novel insights into protein dimerization and multifunctionality. Biochimica Et Biophysica Acta-Proteins and Proteomics, 2015. 1854(5): p. 492-504.

33. Breydo, L., Newland, B., Zhang, H., Rosser, A., Werner, C., Uversky, V. N. and Wang, W., *A hyperbranched dopamine-containing PEG-based polymer for the inhibition of alpha-synuclein fibrillation*. Biochemical and biophysical research communications, 2016. 469(4): p. 830-5.

34. Kutyshenko, V. P., Beskaravayny, P. and Uversky, V. N., "In-plant" NMR: Analysis of the Intact Plant Vesicularia dubyana by High Resolution NMR Spectroscopy. Molecules, 2015. 20(3): p. 4359-4368.

35. Uversky, V. N., The multifaceted roles of intrinsic disorder in protein complexes. Febs Letters, 2015. 589 (19): p. 2498-2506.

36. Portillo, A., Hashemi, M., Zhang, Y., Breydo, L., Uyersky, V. N. and Lyubchenko, Y. L., *Role of monomer arrangement in the amyloid self-assembly*. Biochimica Et Biophysica Acta-Proteins and Proteomics, 2015. 1854(3): p. 218-228.

37. Ferreira, L. A., Madeira, P. P., Breydo, L., Reichardt, C., Uversky, V. N. and Zaslaysky, B. Y., *Role of solvent properties of aqueous media in macromolecular crowding effects*. Journal of Biomolecular Structure & Dynamics, 2016. 34(1): p. 92-103.

38. Breydo, L. and Uversky, V. N., *Structural, morphological, and functional diversity of amyloid oligomers*. Febs Letters, 2015. 589(19): p. 2640-2648.

39. Calcul, L., Zhang, B., Jinwal, U. K., Dickey, C. A. and Baker, B. J., *Natural products as a rich source of tau-targeting drugs for Alzheimer's disease*. Future Med Chem, 2012. 4(13): p. 1751-61.

40. Doig, A. J. and Derreumaux, P., *Inhibition of protein aggregation and amyloid formation by small molecules*. Current Opinion in Structural Biology, 2015. 30: p. 50-56.

41. Hu, P., Li, Z., Chen, M., Sun, Z., Ling, Y., Jiang, J. and Huang, C., Structural elucidation and protective role of a polysaccharide from *Sargassum fusiforme* on ameliorating learning and memory deficiencies in mice. Carbohydrate Polymers, 2016. 139: p. 150-158.

42. Liu, H., Ojha, B., Morris, C., Jiang, M., Wojcikiewicz, E. P., Rao, P. P. N. and Du, D., *Positively Charged Chitosan and N-Trimethyl Chitosan Inhibit A beta Fibrillogenesis*. Biomacromolecules, 2015. 16(8): p. 2363-2373.

43. Zhang, H., Cao, Y., Chen, L., Wang, J., Tian, Q., Wang, N., Liu, Z., Li, J., Wang, N., Wang, X., Sun, P. and Wang, L., *A polysaccharide from Polygonatum sibiricum attenuates amyloid-beta-induced neurotoxicity in PC12 cells*. Carbohydrate Polymers, 2015. 117: p. 879-886.

44. Li, X. Z., Zhang, S. N., Liu, S. M. and Lu, F., *Recent advances in herbal medicines treating Parkinson's disease*. Fitoterapia, 2013. 84: p. 273-85.

45. Caruana, M. and Vassallo, N., *Tea Polyphenols in Parkinson's Disease*. Adv Exp Med Biol, 2015. 863: p. 117-37.

46. Fazili, N. A. and Naeem, A., Anti-fibrillation potency of caffeic acid against an antidepressant induced fibrillogenesis of human alpha-synuclein: Implications for Parkinson's disease. Biochimie, 2015. 108: p. 178-85.

47. Goldberg, M. S. and Lansbury, P. T., Jr., Is there a cause-and-effect relationship between alpha-synuclein fibrillization and Parkinson's disease? Nat Cell Biol, 2000. 2(7): p. E115-119.

48. Fink, A. L., *The aggregation and fibrillation of alpha-synuclein*. Acc Chem Res, 2006. 39(9): p. 628-34.

49. Breydo, L., Wu, J. W. and Uversky, V. N., *Alpha-synuclein misfolding and Parkinson's disease*. Biochim Biophys Acta, 2012. 1822(2): p. 261-85.

50. Vassar, P. S. and Culling, C. F., Fluorescent stains, with special reference to amyloid and connective tissues. Arch Pathol, 1959. 68: p. 487-98.

51. Biancalana, M. and Koide, S., *Molecular mechanism of Thioflavin-T binding to amyloid fibrils*. Biochim Biophys Acta, 2010. 1804(7): p. 1405-12.

52. Uversky, V. N. and Eliezer, D., *Biophysics of Parkinson's disease: structure and aggregation of alpha-synuclein*. Curr Protein Pept Sci, 2009. 10(5): p. 483-99.

53. Alcantar N A, Aydil E S and Israelachvili N J, *Polyethylene glycol coated biocompatible surfaces*. J Biomed Mater Res, 2000. 51(3): p. 343-351.

54. Drummond, C., Alcantar, N. and Israelachvili, J., *Shear alignment of confined hydrocarbon liquid films*. Physical Review E, 2002. 66(1).

55. Chittur K K, FTIR/ATR for protein adsoption to biomaterial surfaces. Biomaterials, 1997. 19: p. 357-369.

56. Goormaghtigh, E., Raussens, V. and Ruysschaert, J. M., *Attenuated total reflection infrared spectroscopy of proteins and lipids in biological membranes*. Biochimica Et Biophysica Acta-Reviews on Biomembranes, 1999. 1422 (2): p. 105-185.

57. Sarroukh, R., Cerf, E., Derclaye, S., Dufrene, Y. F., Goormaghtigh, E., Ruysschaert, J.-M. and Raussens, V., *Transformation of amyloid beta (1-40) oligomers into fibrils is characterized by a major change in secondary structure*. Cellular and Molecular Life Sciences, 2011. 68(8): p. 1429-1438.

58. Sarroukh, R., Goormaghtigh, E., Ruysschaert, J.-M. and Raussens, V., ATR-FTIR: A "*rejuvenated*" tool to investigate amyloid proteins. Biochimica Et Biophysica Acta-Biomembranes, 2013. 1828(10): p. 2328-2338.

59. Singh, B. R., Infrared Analysis of Peptides and Proteins, Principles and Applications, ed. A. S. S. 750. 2000, Washington, D.C.

60. Byler D M, S. H., Examination of the secondary structure of proteins by deconvolved FTIR spectra. Biopolymers, 1986. 25: p. 469-487.

61. Walsh, D. M., Hartley, D. M., Kusumoto, Y., Fezoui, Y., Condron, M. M., Lomakin, A., Benedek, G. B., Selkoe, D. J. and Teplow, D. B., *Amyloid beta protein fibrillogenesis-Structure and biological activity of protofibrillar intermediates*. Journal of Biological Chemistry, 1999. 274(36): p. 25945-25952.

62. Stine, W. B., Dahlgren, K. N., Krafft, G. A. and LaDu, M. J., In vitro *characterization of conditions for amyloid-beta peptide oligomerization and fibrillogenesis*. Journal of Biological Chemistry, 2003. 278(13): p. 11612-11622.

63. Dahlgren, K. N., Manelli, A. M., Stine, W. B., Baker, L. K., Krafft, G. A. and LaDu, M. J., *Oligomeric and fibrillar species of amyloid-beta peptides differentially affect neuronal viability*. Journal of Biological Chemistry, 2002. 277(35): p. 32046-32053.

64. Jimenez, J., M. S. Thesis (Major Professor: Norma Alcantar): Systematic study of amyloid beta peptide conformations implications for AD. Vol. M.S. 2005, Tampa: USF.

65. Selenica, M. L., Wang, X., Ostergaard-Pedersen, L., Westlind-Danielsson, A. and Grubb, A., *Cystatin C reduces the in vitro formation of soluble A beta 1-42 oligomers and protofibrils*. Scandinavian Journal of Clinical & Laboratory Investigation, 2007. 67(2): p. 179-190.
66. Alcantar, N. A., Joseph, B. and Young, K., *Patent: Water purification method using plant molecules for removal of arsenic*. 2011 (U.S. Pat. No. 7,943,049B1): University of South Florida, USA.
67. Sluiter, J. B., Ruiz, R. O., Scarlata, C. J., Sluiter, A. D. and Templeton, D. W., *Compositional Analysis of Lignocellulosic Feedstocks. 1. Review and Description of Methods*. Journal of Agricultural and Food Chemistry, 2010. 58(16): p. 9043-9053.
68. Foster, C. E., Martin, T. M. and Pauly, M., *Comprehensive compositional analysis of plant cell walls (Lignocellulosic biomass) part 1: lignin*. Journal of visualized experiments: JoVE, 2010(37).
69. Foster, C. E., Martin, T. M. and Pauly, M., Comprehensive compositional analysis of plant cell walls (lignocellulosic biomass) part II: carbohydrates. Journal of visualized experiments: JoVE, 2010(37).
70. Wong, C. H. and Whitesides, G. M., *Synthesis of sugars by Aldolase-Catalyzed Condensation-reactions* Journal of Organic Chemistry, 1983. 48(19): p. 3199-3205.
71. Nishiyama, T., Kajimoto, T., Mohile, S. S., Hayama, N., Otsuda, T., Ozeki, M. and Node, M., The first enantioselective synthesis of imino-deoxydigitoxose and protected imino-digitoxose by using L-threonine aldolase-catalyzed aldol condensation. Tetrahedron-Asymmetry, 2009. 20(2): p. 230-234.
72. Kajimoto, T., *Synthesis of carbohydrate related compounds by using aldolase catalyzed reaction*. Yakugaku Zasshi-Journal of the Pharmaceutical Society of Japan, 2000. 120(1): p. 42-53.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method of treating an amyloid disease, comprising the steps:
   identifying a patient suffering from an amyloid disease;
   obtaining a plant mucilage extract, wherein the plant mucilage extract is gelling extract or non-gelling extract from *Opuntia ficus-indica;*
   wherein the gelling extract is formed by steps comprising:
   obtaining cactus pads;
   dicing and boiling the cactus pads;
   liquidizing the cactus pads and adding a base to neutralize the liquidized cactus pads;
   centrifuging the liquidized cactus pads into a liquid fraction and a solid precipitate;
   collecting the solid precipitate;
   adding sodium hexametaphosphate to the solid precipitate and mixing;
   filtering the solid precipitate;
   resuspending the solid precipitate in deionized water to form a suspension;
   lowering the pH of the suspension;
   precipitating a mucilage precipitate from the suspension;
   resuspending the mucilage precipitate with water and adjusting the pH until the mucilage precipitate dissolves; and
   filtering the dissolved mucilage precipitate to form the gelling extract;
   wherein the non-gelling extract is formed by steps comprising:
   obtaining cactus pads;
   dicing and boiling the cactus pads;
   liquidizing the cactus pads and adding a base to neutralize the liquidized cactus pads;
   centrifuging the liquidized cactus pads into a liquid fraction and a solid precipitate;
   collecting the liquid fraction;
   adding sodium chloride to the liquid fraction and mixing;
   filtering the liquid fraction to form a filtrate;
   adding acetone or isopropanol to the filtrate to form a mucilage precipitate;
   washing the precipitate; and
   drying the precipitate to form the non-gelling extract; and
   administering the plant mucilage extract to the patient.

2. The method of treating an amyloid disease, according to claim 1 further comprising:
   administering the plant mucilage extract into a central nervous system of the patient.

3. The method of claim 2, wherein the plant mucilage extract is administered into the central nervous system using a pump.

4. The method of claim 2, wherein the amyloid disease is Alzheimer's disease or Parkinson's disease.

* * * * *